United States Patent
Davis et al.

(10) Patent No.: US 10,456,463 B2
(45) Date of Patent: Oct. 29, 2019

(54) VACCINES COMPRISING CHOLESTEROL AND CPG AS SOLE ADJUVANT-CARRIER MOLECULES

(75) Inventors: Heather Lynn Davis, Ottawa (CA); Risini Weeratna, Ottawa (CA); Paul J. Dominowski, Kalamazoo, MI (US)

(73) Assignee: Zoetis Belgium S.A, Brussels (BE)

( * ) Notice: Subject to any disclaimer, the term of this patent is extended or adjusted under 35 U.S.C. 154(b) by 330 days.

(21) Appl. No.: 13/699,997

(22) PCT Filed: May 27, 2011

(86) PCT No.: PCT/IB2011/052347
§ 371 (c)(1),
(2), (4) Date: Nov. 26, 2012

(87) PCT Pub. No.: WO2011/148356
PCT Pub. Date: Dec. 1, 2011

(65) Prior Publication Data
US 2013/0084306 A1  Apr. 4, 2013

Related U.S. Application Data

(60) Provisional application No. 61/349,244, filed on May 28, 2010.

(51) Int. Cl.
*A61K 39/385* (2006.01)
*A61K 45/00* (2006.01)
(Continued)

(52) U.S. Cl.
CPC ............ *A61K 39/39* (2013.01); *A61K 39/099* (2013.01); *A61K 39/12* (2013.01); *A61K 39/155* (2013.01); *A61K 39/265* (2013.01); *A61K 2039/5252* (2013.01); *A61K 2039/5254* (2013.01); *A61K 2039/55505* (2013.01); *A61K 2039/55555* (2013.01); *A61K 2039/55561* (2013.01);
(Continued)

(58) Field of Classification Search
None
See application file for complete search history.

(56) References Cited

U.S. PATENT DOCUMENTS 6,610,308 B1 * 8/2003 Haensler ............... A61K 39/39
424/184.1
6,936,255 B1 * 8/2005 Wettendorff ............. 424/204.1
(Continued)

FOREIGN PATENT DOCUMENTS

WO   WO 9602555 A1 *  2/1996 ............. A61K 31/70
WO   2003/028760   4/2003
(Continued)

OTHER PUBLICATIONS

Muderwha et al., "Oil in Water Liposomal Emulsions: Characterization and Potential Use in Vaccine Delivery," Journal of Pharmaceutical Sciences, vol. 88, No. 12: 1332-1339 (1999).*
(Continued)

*Primary Examiner* — M Franco G Salvoza
(74) *Attorney, Agent, or Firm* — Vyacheslav Vasilyev

(57) ABSTRACT

Described are vaccines having one or more antigens cholesterol and CpG. Aspects of the invention relate to the use of the vaccines of the invention for the treatment and/or prevention of human and animal disorders.

20 Claims, 9 Drawing Sheets

Specification includes a Sequence Listing.

(51) Int. Cl.
    *A61K 39/39*     (2006.01)
    *A61K 39/02*     (2006.01)
    *A61K 39/12*     (2006.01)
    *A61K 39/155*     (2006.01)
    *A61K 39/265*     (2006.01)
    *A61K 39/00*     (2006.01)

(52) U.S. Cl.
CPC ............. *A61K 2039/55577* (2013.01); *A61K 2039/60* (2013.01); *A61K 2039/6037* (2013.01); *A61K 2039/70* (2013.01); *C12N 2710/16734* (2013.01); *C12N 2760/18534* (2013.01); *C12N 2760/18634* (2013.01); *C12N 2770/24334* (2013.01); *C12N 2770/32334* (2013.01)

(56) References Cited

U.S. PATENT DOCUMENTS

| | | | |
|---|---|---|---|
| 7,049,302 | B1 | 5/2006 | Kensil |
| 2002/0055477 | A1* | 5/2002 | Nest .................. A61K 9/1647 514/44 R |
| 2002/0058047 | A1* | 5/2002 | Garcon et al. ............. 424/283.1 |
| 2005/0175630 | A1* | 8/2005 | Raz et al. ................... 424/203.1 |
| 2005/0266015 | A1* | 12/2005 | Clerici .................. A61K 39/21 424/188.1 |
| 2006/0019923 | A1* | 1/2006 | Davis .................. A61K 31/337 514/44 A |
| 2006/0189550 | A1* | 8/2006 | Jiang .................. A61K 39/0011 514/26 |
| 2007/0212329 | A1* | 9/2007 | Bruck et al. ................. 424/85.2 |
| 2007/0253979 | A1* | 11/2007 | Moss .................. A61K 39/12 424/208.1 |
| 2008/0254065 | A1* | 10/2008 | Podda et al. ................ 424/206.1 |
| 2009/0017075 | A1* | 1/2009 | Van Nest ............. A61K 9/0014 424/275.1 |
| 2009/0324641 | A1 | 12/2009 | Dominowski et al. |
| 2010/0166780 | A1 | 7/2010 | Debelak et al. |
| 2011/0038941 | A1* | 2/2011 | Lee ........................ C12N 15/88 424/498 |

FOREIGN PATENT DOCUMENTS

| | | |
|---|---|---|
| WO | 2005/039634 | 5/2005 |
| WO | 2009/156960 | 12/2009 |

OTHER PUBLICATIONS

Baudner et al., "MF59 Emulsion Is an Effective Delivery System for a Synthetic TLR4 Agonist (E6020)," Pharmaceutical Research, vol. 26, No. 6 (2009).*
Kirby et al., "Effect of the Cholesterol Content of Small Unilamellar Liposomes on their Stability in vivo and in vitro," Biochem. J. 186: 591-598 (1980).*
Kandimalla et al., "A dinucleotide motif in oligonucleotides shows potent immunomodulatory activity and overrides species-specific recognition observed with CpG motif," PNAS vol. 100, No. 24: 14303-14308 (2003).*
Lytle et al., "Predicted Inactivation of Viruses of Relevance to Biodefense by Solar Radiation," J. Virol. 79(22): 14244 (2005).*
Yelamaggad et al., "Cholesterol-based nonsymmetric liquid crystal dimers: an overview," Journal of Material Chemistry, 18, 2927-2949 (2008).*
Hemmi et al., "A Toll-like receptor recognizes bacterial DNA," Nature, vol. 408: 740-745 (2000).*
Nour et al., "Demulsification of Virgin Coconut Oil by Centrifugation Method: A Feasibility Study," International Journal of Chemical Technology 1(2): 59-64 (2009).*
Lechmann et al., "Hepatitis C Virus-Like Particles Induce Virus-Specific Humoral and Cellular Immune Response in Mice," Hepatology, vol. 34, No. 2: 417-423 (2001).*
Farhood et al., "Cationic Liposomes for Direct Gene Transfer in Therapy of Cancer and Other Diseases," Ann NY Acad Sci 716: 23-34 (1994).*
Insua et al., "IMT504, the Prototype of the Immunostimulatory Oligonucleotide of the PyNTTTTGT Class, Increases the Number of Progenitors of Mesenchymal Stem Cells Both In Vitro and In Vivo: Potential Use in Tissue Repair Therapy," Stem Cells 25:1047-1054 (2007).*
Yu et al., "Immunostimulatory properties of phosphorothioate CpG DNA containing both 3'-5'—and 2'-5'-internucleotide linkages," Nucleic Acids Research vol. 30, No. 7: 1613-1619 (2002).*
Ryte et al., "Interaction of cholesterol-conjugated alkylating oligonucleotide derivatives with cellular biopolymers," FEBS vol. 299, No. 2, :124-126 (1992).*
Stewart-Tull, "Adjuvant Formulations for Experimental Vaccines," Methods in Molecular Medicine, vol. 87: Vaccine Protocols, 2nd ed. (2003).*
Davis et al., "Liposomes as adjuvants with immunopurified tetanus toxoid: influence of liposomal characteristics," Immunology 61: 229-234 (1987).*
Gao et al., "A novel cationic liposome reagent for efficient transfection of mammalian cells," Biochem Biophys Res Commun. 179(1):280-285 (1991)(abstract only).*
PCT International Search Report, PCT/IB2011/052347, dated Oct. 7, 2011 (5 pages).
Lechmann et al., "Hepatitis C Virus-Like Particles Induce Virus-Specific Humoral and Cellular Immune Responses in Mice", Hepatology, 34:417-423, 2001.

* cited by examiner

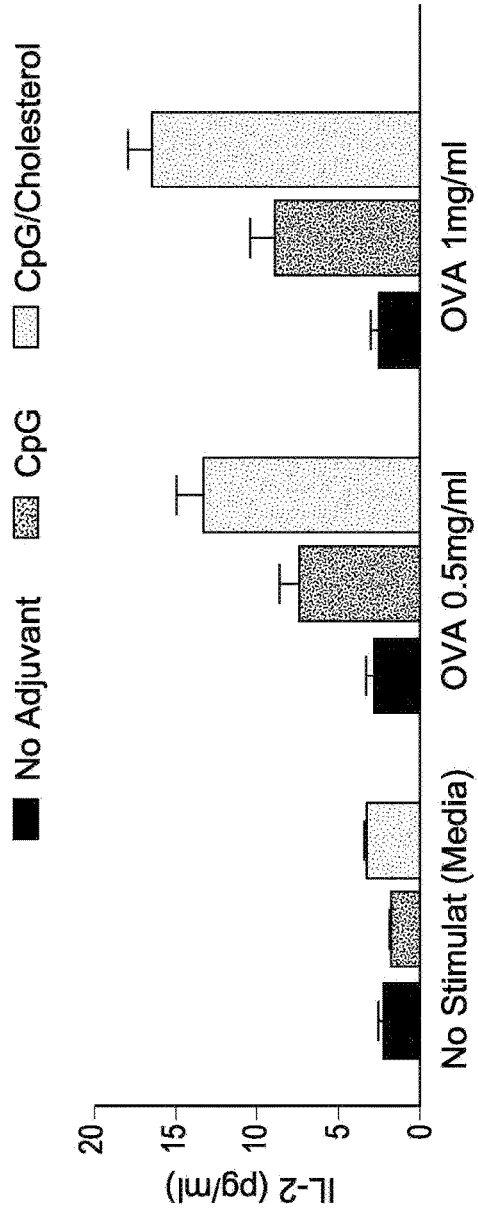
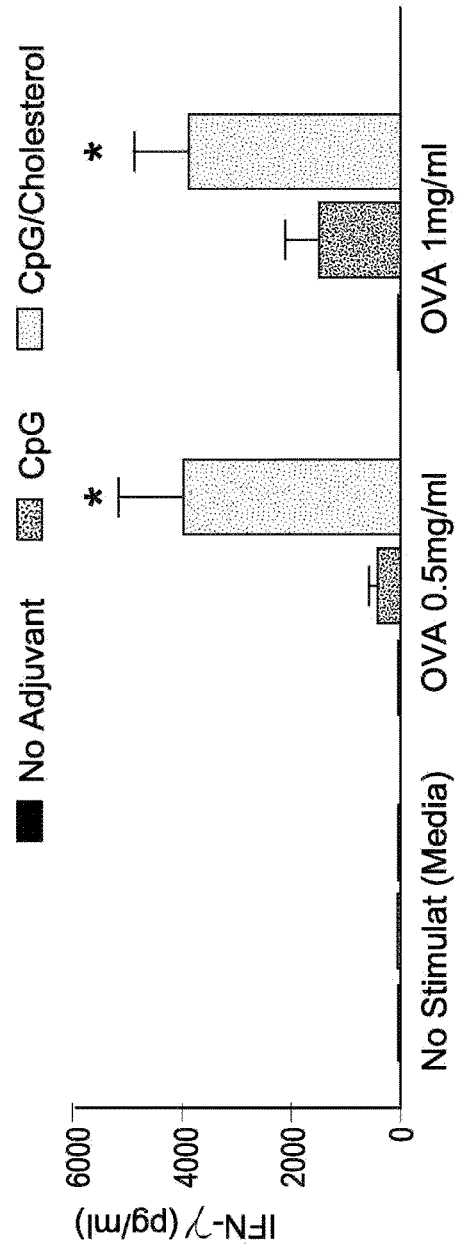
FIG. 2A
FIG. 2B

VACCINES COMPRISING CHOLESTEROL AND CPG AS SOLE ADJUVANT-CARRIER MOLECULES

This application claims priority to U.S. provisional patent application No. 61/349,244, filed on May 28, 2010, hereby incorporated by reference in its entirety.

FIELD OF THE INVENTION

The invention relates to vaccines having one or more antigens and cholesterol and uses thereof. The invention further relates to vaccines having one or more antigens and one or more immune modulatory molecules and cholesterol and uses thereof.

BACKGROUND OF THE INVENTION

It has been discovered that cholesterol can potentate the activity of immune modulatory molecules and therefore the combination of cholesterol and immune modulatory molecules can be used in the treatment and/or prevention of human and animal disorders. Vaccines comprising one or more antigens and cholesterol, and vaccines comprising one or more antigens, one or more immune modulatory molecules and cholesterol are described.

SUMMARY OF THE INVENTION

In certain aspects, the invention relates to a vaccine comprising one or more antigens and cholesterol. In some aspects, the one or more antigens are each independently, a microbial antigen, a self antigen, a tumor antigen, an allergen, or an addictive substance.

In certain aspects, the invention relates to a vaccine comprising one or more antigens and one or more immune modulatory molecules and cholesterol. In aspects the vaccine further comprises a pharmaceutical carrier. In some aspects, the one or more antigens are each independently, a microbial antigen, a self antigen, a tumor antigen, an allergen, or an addictive substance.

In certain aspects, the invention relates to a method of inducing an antigen-specific immune response in a subject in need thereof, comprising administering a vaccine comprising one or more antigens and cholesterol in an effective amount to induce an antigen-specific immune response in the subject.

In certain aspects, the invention relates to a method of inducing an antigen-specific immune response in a subject in need thereof, comprising administering a vaccine comprising one or more antigens and one or more immune modulatory molecules and cholesterol.

DESCRIPTION OF FIGURES

FIG. 1: Graphs representing antigen specific cytokine secretion by T cells in the presence of no adjuvant, or in the presence of CpG or CpG+cholesterol as an adjuvant.

FIG. 2: Graph of IL-2 (FIG. 2a) and IFN-γ (FIG. 2b) production in the presence of no adjuvant, CpG and CpG+cholesterol.

FIG. 3: Graph of ovalbumin specific CD8+ T cell responses in the presence of no adjuvant or in the presence of CpG or CpG+cholesterol as an adjuvant.

DESCRIPTION OF SEQUENCES

Figure 1A:
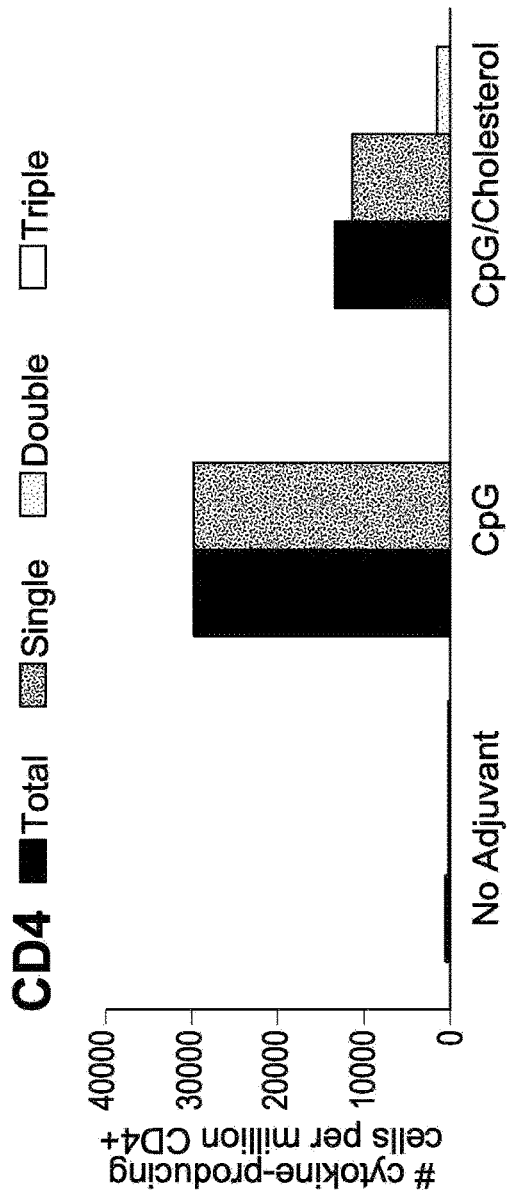
FIG. 1a. Graph of CD4+ T cells secreting single or double cytokines.
Figure 1B:
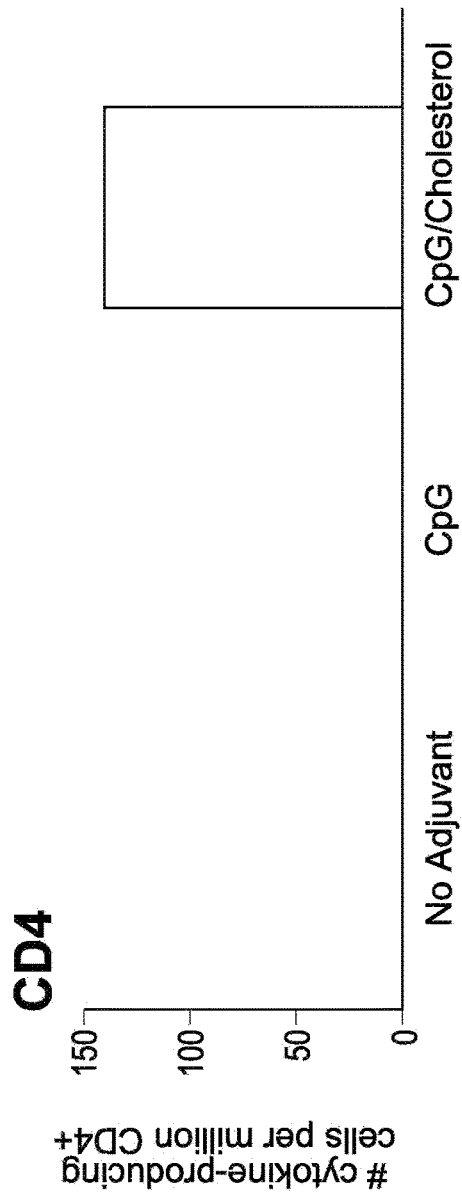
FIG. 1b. Graph of CD4+ T cells secreting triple cytokines.

SEQ ID NO: 1 -
CPG 7909
5' TCGTCGTTTTGTCGTTTTGTCGTT 3'.

SEQ ID NO: 2 -
CpG 24555
5' TCGTCGTTTTTCGGTGCTTTT 3'.

SEQ ID NO: 3 -
CPG 10104
5' TCGTCGTTTCGTCGTTTTGTCGTT 3'.

SEQ ID NO: 4 -
CPG 10101
5' TCGTCGTTTTCGGCGGCCGCCG 3'.

SEQ ID NO: 5 -
CPG 10109
5' TCGTC-GTTTTAC-GGCGCC-GTCCCG 3'.

SEQ ID NO: 6 -
CpG 23407
5' T*C-G*T*C*G*T*T*T*T*C*G*G*C*G*C*G*C*G*C*C*G*T 3'.

SEQ ID NO: 7 -
CPG 21798
5' T*C-G*T*C-G*A*C-G*A*T*C-G*G*C*G*C-G*C*G*C*C*G 3'.

SEQ ID NO: 8 -
CPG 23430
5' T*C-G*A*C*G*T*C*G*A*T*C*G*G*C*G*C*G*C*G*C*C*G 3'.

-continued

SEQ ID NO: 9 -
CpG 24558
5' T*C*G*A*C*G*T*C*G*A*T*C*G*G*C*G*C*G*C*C*G*T 3'.

SEQ ID NO: 10 -
CPG 23871
5' JU*C-G*A*C*G*T*C*G*A*T*C*G*G*C*G*C*G*C*C*G 3'.

SEQ ID NO: 11 -
CPG 23873
5' JU*C-G*A*C*G*T*C*G*A*T*C*G*G*C*G*C*G*C*C*G*T* 3'.

SEQ ID NO: 12 -
CPG 23874
5' *C*G*A*C*G*T*C*G*A*T*C*G*G*C*G*C*G*C*C*G*T 3'.

SEQ ID NO: 13 -
CPG 23875
5' EU*C-G*A*C*G*T*C*G*A*T*C*G*G*C*G*C*G*C*C*G 3'.

SEQ ID NO: 14 -
CpG 23877
5' JU*C-G*T*C*G*A*C*G*A*T*C*G*G*C*G*G*C*C*G*C*G*T 3'.

SEQ ID NO: 15 -
CpG 23878
5' JU*C*G*T*C*G*A*C*G*A*T*C*G*G*C*G*G*C*C*G*C*G*T 3'.

SEQ ID NO: 16 -
poly I:
C ODN1a 5'- ICI CIC ICI CIC ICI CIC ICI CIC IC-3'.

SEQ ID NO: 17 -
5' GGGGACGACGTCGTGGGGGGG 3'.

SEQ ID NO: 18 -
5' G*G*G_G_A_C_G_A_C_G_T_C_G_T_G_G*G*G*G*G 3'.

SEQ ID NO: 19 -
5' TCGTCGTTTTGTCGTTTGTCGTT 3'.

SEQ ID NO: 20 -
5' TCGTCGTTTTGTCGTTTTTTCGA 3'.

SEQ ID NO: 21 -
5' T*C*G*T*C*G*T*T*T*T*T*C*G*G*T*G*C*T*T*T*T 3'.

SEQ ID NO: 22 -
5' T*C*G*T*C*G*T*T*T*T*T*T*C*G*G*T*C*G*T*T*T*T 3'.

SEQ ID NO: 23 -
5' T*C*G*T*C*G*T*T*T*T*T*G*T*C*G*T*T*T*T*G*T*C*G*T*T 3'.

SEQ ID NO: 24 -
5' T*C*G*T*C*G*T*T*T*C*G*T*C*G*T*T*T*T*G*T*C*G*T*T 3'.

SEQ ID NO: 25 -
5' T*C*G*T*C*G*T*T*T*T*G*T*C*G*T*T*T*T*T*T*C*G*A 3'.

SEQ ID NO: 26 -
5' TCGCGTCGTTCGGCGCGCGCCG 3'.

SEQ ID NO: 27 -
5' TCGTCGACGTTCGGCGCGCGCCG 3'.

SEQ ID NO: 28 -
5' TCGGACGTTCGGCGCGCGCCG 3'.

SEQ ID NO: 29 -
5' TCGGACGTTCGGCGCGCCG 3'.

SEQ ID NO: 30 -
5' TCGCGTCGTTCGGCGCGCCG 3'.

SEQ ID NO: 31 -
5' TCGACGTTCGGCGCGCGCCG 3'.

SEQ ID NO: 32 -
5' TCGACGTTCGGCGCGCGG 3'.

SEQ ID NO: 33 -
5' TCGCGTCGTTCGGCGCCG 3'.

SEQ ID NO: 34 -
5' TCGCGACGTTCGGCGCGCGCCG 3'.

SEQ ID NO: 35 -
5' TCGTCGTTTTCGGCGCGCGCCG 3'.

SEQ ID NO: 36 -
5' TCGTCGACGATCGGCGCGCGCCG 3'.

SEQ ID NO: 37 -
5' T*C_G*T*C_G*A*C_G*A*T*C_G*G*C*G_G*C*G*C*C_G 3'.

SEQ ID NO: 38 -
5' T*C_G*C_G*T*C_G*T*T*C_G*G*C*G*C_G*C*G*C*C_G 3'.

SEQ ID NO: 39 -
5' T*C_G*T*C_G*A*C_G*T*T*C_G*G*C*G*C_G*C*G*C*C_G 3'.

SEQ ID NO: 40 -
5' T*C_G*G*A*C_G*T*T*C_G*G*C*G*C_G*C*G*C*C*G 3'.

SEQ ID NO: 41 -
5' T*C_G*G*A*C_G*T*T*C_G*G*C*G*C*G*C*C_G 3'.

SEQ ID NO: 42 -
5' T*C_G*C_G*T*C_G*T*T*C_G*G*C*G*C_G*C*C_G 3'.

SEQ ID NO: 43 -
5' T*C_G*A*C_G*T*T*C_G*G*C*G*C_G*C*G*C*C_G 3'.

SEQ ID NO: 44 -
5' T*C_G*A*C_G*T*T*C_G*G*C*G*C*G*C*C_G 3'.

SEQ ID NO: 45 -
5' T*C_G*C_G*T*C_G*T*T*C_G*G*C*G*C*C_G 3'.

SEQ ID NO: 46 -
5' T*C_G*C_G*A*C_G*T*T*C_G*G*C*G*C_G*C*G*C*C_G 3'.

SEQ ID NO: 47 -
5' T*C*G*T*C*G*T*T*T*T*C*G*G*C*G*C*G*C*G*C*C*G 3'.

-continued

SEQ ID NO: 48 -
5' T*C*G*T*C*G*T*T*T*T*C*G*G*C*G*G*C*C*G*C*C*G 3'.

SEQ ID NO: 49 -
5' T*C*G*T*C_G*T*T*T*T*A*C_G*G*C*G*C*C_G*T*G*C*C*G 3'.

SEQ ID NO: 50 -
5' T*C_G*T*C*G*T*T*T*T*C*G*G*C*G*C*G*C*G*C*C*G*T 3'.

(*) represents the presence of a stabilized internucleotide linkage and _ represents a phosphodiester bond. J represents an iodo modified nucleotide and E represents an ethyl modified nucleotide.

DETAILED DESCRIPTION OF THE INVENTION

Aspects of the invention relate to vaccines having one or more antigens and cholesterol, and vaccines having one or more antigens and one or more immune modulatory molecules and cholesterol. In aspects of the invention, methods of inducing an antigen-specific immune response in a subject in need thereof by administering the vaccines of the invention are disclosed. Use of the vaccines in the manufacture of a medicament for the treatment of a disorder are also disclosed.

In aspects of the invention, a one or more antigen(s) are each independently, a microbial antigen, a self antigen, a tumor antigen, an allergen, or an addictive substance. In some aspects, a microbial antigen is of bacterial, viral or parasitic origin. In some aspects, the antigen is a peptide, a peptide conjugated to a carrier protein, a polypeptide, a recombinant protein, a purified protein, whole killed pathogen, live attenuated virus, live attenuated bacteria, antigen expressed within a viral or bacterial vector, a polysaccharide, a polysaccharide conjugated to a carrier protein, protein conjugated to a virus-like particle, a hapten, a hapten conjugated to a carrier protein or a small molecule.

In aspects of the invention, the antigen is of bacterial origin. In some aspects, the bacterial antigen is whole killed bacteria, live attenuated bacteria or bacterial purified proteins.

In aspects of the invention, a bacteria includes, but is not limited to, *Aceinetobacter caicoaceticus, Acetobacter paseruianus, Actinobacillus actinomycetemcomitans, Actinobacillus pleuropneumoniae, Actinomyces israelii, Actinomyces viscosus, Aeromonas hydrophila, Aicaliges eutrophus, Alicyclobacillus acidocaldarius, Arhaeglobus fulgidus, Bacillus* species, *Bacillus antracis, Bacillus pumilus, Bacillus stearothermophillus, Bacillus subtilis, Bacillus thermocatenulatus, Bacteroides* species, *Bordetella* species, *Bordetella bronchiseptica, Borrelia burgdorferi, Brucella* species, *Burkholderia cepacia, Burkholderia glumae, Brachyspira* species. *Brachyspira hyodysenteria, Brachyspira pilosicoli, Camphylobacter* species, *Campylobacter coli, Campylobacter fetus, Campylobacter hyointestinalis, Campylobacter jejuni, Chlamydia psittaci, Chlamydia trachomatis, Chlamydophila* species, *Chromobacterium viscosum, Clostridium* species, *Clostridium botulinum, Clostridium difficile, Clostridium perfringens, Clostridium tetani, Corynebacterium* species, *Corynebacterium diphtheriae, Ehrlichia canis, Enterobacter* species, *Enterobacter aerogenes, Enterococcus* species, *Erysipelothrix rhusiopathieae, Escherichia* species, *Escherichia coli, Fusobacterium nucleatum, Haemophilus* species, *Haemophilus influenzae, Haemophilus somnus, Helicobacter* species, *Helicobacter pylori, Helicobacter suis, Klebsiella* species, *Klebsiella pneumoniae, Lactobacillus acidophilis, Lawsonia intracellularis, Legionella* species, *Legionella pneumophilia, Leptospira* species, such as *Leptospira canicola, Leptospira grippotyposa, Leptospira hardjo, Leptospira borgpetersenii hardjo-bovis, Leptospira borgpetersenii hardjo-prajitno, Leptospira interrogans, Leptospira icterohaemorrhagiae, Leptospira pomona, Leptospira, Leptospira bratislava, Listeria* species, *Listeria monocytogenes,* Meningococcal bacteria, *Moraxella* species, *Mycobacterium* species, *Mycobacterium bovis, Mycobacterium tuberculosis, Mycobacterium avium, Mycobacterium intracellulare, Mycobacterium kansaii, Mycobacterium gordonae, Mycoplasma* species, such as, *Mycoplasma hyopneumoniae, Mycoplasma synoviae, Mycoplasma hyorhinis, Mycoplasma pneumoniae, Mycoplasma mycoides* subsp. mycoides LC, *Neisseria* species, *Neisseria gonorrhoeae, Neisseria meningitidis, Odoribacter denticanis, Pasteurella* species, *Pasteurella (Mannheimia) haemolytica, Pasteurella multocida, Photorhabdus luminescens, Porphyromonas gingivalis, Porphyromonas gulae, Porphyromonas salivosa, Propionibacterium acnes, Proteus* species, *Proteus vulgaris, Pseudomonas* species, *Pseudomnas wisconsinensis, Pseudomonas aeruginosa, Pseudomonas fluorescens* C9, *Pseudomonas fluorescens* SIKW1, *Pseudomonas fragi, Pseudomonas luteola, Pseudomonas oleovorans, Pseudomonas* sp B11-1, *Psychrobacter immobilis, Rickettsia* spp, *Rickettsia prowazekii, Rickettsia rickettsia, Salmonella* species, *Salmonella bongori, Salmonella choleraeuis, Salmonella dublin, Salmonella enterica, Salmonella newport, Salmonella typhimurium, Salmonella typhi, Serratia marcescens, Shigella* species, *Spirlina platensis, Staphylococci* species, *Staphlyoccocus aureus, Staphyloccoccus epidermidis, Staphylococcus hyicus, Streptococcus* species, *Streptobacillus moniliformis,* beta-hemolytic *Streptococcus, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus uberis, Streptococcus dysgalactiae, Streptococcus* (anaerobic sps.), *Streptococcus pneumoniae, Streptococcus mutans, Streptococcus sobrinus, Streptococcus sanguis, Streptomyces albus, Streptomyces cinnamoneus, Streptomyces exfoliates, Streptomyces scabies, Sulfolobus acidocaldarius, Syechocystis* sp., *Treponema* species, *Treponema denticola, Treponema minutum, Treponema palladium, Treponema pertenue, Treponema phagedenis, Treponema refringens, Treponema vincentii, Vibrio* species, *Vibrio cholerae, Yersinia* species and combinations thereof.

Polypeptides or polysaccharides of bacterial pathogens include, but are not limited to, an iron-regulated outer membrane protein (IROMP), an outer membrane protein (OMP), and an A-protein of *Aeromonis salmonicida* which causes furunculosis, p57 protein of *Renibacterium salmoninarum* which causes bacterial kidney disease (BKD), major surface associated antigen (msa), a surface expressed cytotoxin (mpr), a surface expressed hemolysin (ish), and a flagellar antigen of Yersiniosis; an extracellular protein (ECP), an IROMP, and a structural protein of Pasteurellosis; an OMP and a flagellar protein of *Vibrosis anguillarum* and *V. ordalii*; a flagellar protein, an OMP protein, aroA, and purA of *Edwardsiellosis ictaluri* and *E. tarda*; and surface antigen of lchthyophthirius; and a structural and regulatory protein of *Cytophaga columnari*; and a structural and regulatory protein of Rickettsia, IsdA, ClfA, ClfB, Opp3A, HLA and capsular polysaccharides from *Staphylococcus aureus*.

In aspects of the invention, the antigen is of viral origin. In some aspects, the viral antigen is whole killed or inactivated virus, live attenuated virus or viral purified proteins or peptides.

In some aspects, the virus is one that infects animals including, but not limited to, Avian herpesvirus, Avian influenza, Avian leukosis virus, Avian paramyxoviruses, Border disease virus, Bovine coronavirus, Bovine ephemeral fever virus, Bovine herpes viruses, Bovine immunodeficiency virus, Bovine leukemia virus, Bovine parainfluenza virus 3, Bovine respiratory syncytial virus, Bovine viral diarrhea virus (BVDV), BVDV Type I, BVDV Type II, Canine adenovirus, Canine coronavirus (CCV), Canine distemper virus, Canine herpes viruses, Equine herpes viruses, Canine influenza virus, Canine parainffuenza virus, Canine parvovirus, Canine respiratory coronavirus, Classical swine fever virus, Eastern Equine encephalitis virus (EEE), Equine infectious anemia virus, Equine influenza virus, West nile virus, Feline Calicivirus, Feline enteric coronavirus, Feline immunodeficiency virus, Feline infectious peritonitis virus, Feline herpes Virus, Feline influenza virus, Feline leukemia virus (FeLV), Feline viral rhinotracheitis virus, Lentivirus, Marek's disease virus, Newcastle Disease virus, Ovine herpesviruses, Ovine parainfluenza 3, Ovine progressive pneumonia virus, Ovine pulmonary adenocarcinoma virus, Pantropic CCV, Porcine circovirus (PCV) Type I, PCV Type II, Porcine epidemic diarrhea virus, Porcine hemagglutinating encephalomyletitis virus, Porcine herpesviruses, Porcine parvovirus, Porcine reproductive and respiratory syndrome (PRRS) Virus, Pseudorabies virus, Rabies, Rotovirus, Rhinoviruses, Rinderpest virus, Swine influenza virus, Transmissible gastroenteritis virus, Turkey coronavirus, Venezuelan equine encephalitis virus, Vesicular stomatitis virus, West Nile virus, Western equine encephalitis virus and combinations thereof.

In some aspects, the virus is one that infects humans, including, but not limited to, Adenoviridae (most adenoviruses); Arena viridae (hemorrhagic fever viruses); Astroviruses; Bungaviridae (e.g., Hantaan viruses, bunga viruses, phleboviruses and Nairo viruses); Calciviridae (e.g., strains that cause gastroenteritis); Coronoviridae (e.g., coronaviruses); Filoviridae (e.g., ebola viruses); Flaviridae (e.g., hepatitis C virus, dengue viruses, encephalitis viruses, yellow fever viruses); Hepadnaviridae (Hepatitis B virus); Herpesviridae (herpes simplex virus (HSV) 1 and 2, varicella zoster virus, cytomegalovirus (CMV), herpes virus); Iridoviridae (e.g., African swine fever virus); Norwalk and related viruses; Orthomyxoviridae (e.g., influenza viruses); Papovaviridae (papilloma viruses, polyoma viruses); Paramyxoviridae (e.g., parainfluenza viruses, mumps virus, measles virus, respiratory syncytial virus); Parvovirida (parvoviruses); Picornaviridae (e.g., polio viruses, hepatitis A virus; enteroviruses, human Coxsackie viruses, rhinoviruses, echoviruses); Poxyiridae (variola viruses, vaccinia viruses, pox viruses); Reoviridae (e.g., reoviruses, orbiviurses and rotaviruses); Retroviridae (e.g. human immunodeficiency viruses, such as HIV-tor HIV-2 (also referred to as HTLV-III, LAV or HTLV-III/LAV, or HIV-III; and other isolates, such as HIV-LP); Rhabdoviradae (e.g., vesicular stomatitis viruses, rabies viruses); Togaviridae (e.g., equine encephalitis viruses, rubella viruses); and Unclassified viruses (e.g., the etiological agents of Spongiform encephalopathies, the agent of delta hepatitis (thought to be a defective satellite of hepatitis B virus).

In aspects of the invention, the antigen is of parasitic origin. In some aspects, the parasite is a protein from *Anaplasma, Ancylostoma* (hookworms), *Ascaris, Babesia, Coccidia, Cryptosporidium parvum, Dirofilaria* (heartworms), *Eimeria* species, *Fasciola hepatica* (liver fluke), *Giardia, Hammondia, Isopsora, Leishmania* species, *Neospora caninum, Sarcocystis, Schistosoma, Strongyloides, Taenia, Toxoplasma gondii, Trichinella* species, *Trichomonas* species or *Trypanosoma* species. and combinations thereof.

In some aspects, the parasite is an external parasite. In some aspects, an external parasite includes, but is not limited to, ticks, including *Ixodes, Rhipicephalus, Dermacentor, Amblyomma, Boophilus, Hyalomma,* or *Haemaphysalis* species, and combinations thereof.

In aspects of the invention, an antigen is a self antigen. In some aspects, a self antigen is an antigen of a subject's own cells or cell products that causes an immune response in a subject. In some aspects, a self antigen includes, but is not limited to, a tumor antigen, an antigen associated with Alzheimer's Disease, an antigen against an antibody, or an antigen that is expressed from human endogenous retroviral elements. An antigen associated with Alzheimer's Disease may be tau or β-amyloid. An antigen against an antibody may be an antigen against a human antibody, for example, in some embodiments the antigen is IgE.

In aspects of the invention, an antigen is a tumor antigen. In some aspects, the tumor antigen is one or more of WT1, MUC1, LMP2, HPV E6 or HPV E7, EGFR or variant form, for example, EGFRvIII, HER-2/neu, Idiotype, MAGE A3, p53 nonmutant, NY-ESO-1, PSMA, GD2, CEA, MelanA/MART1, Ras mutant, gp100, p53 mutant, Proteinase3 (PR1), bcr-abl, Tyrosinase, Survivin, PSA, hTERT, Sarcoma translocation breakpoints, EphA2, PAP, ML-IAP, AFP, EpCAM, ERG (TMPRSS2 ETS fusion gene), NM 7, PAX3, ALK, Androgen receptor, Cyclin B1, polysialic acid, MYCN, RhoC, TRP-2, GD3, Fucosyl GM1, Mesothelin, PSCA, MAGE A1, sLe (animal), CYP1B1, PLAC1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, B7H3, Legumain, Tie 2, Page4, VEGFR2, MAD-CT-1, FAP, PDGFR-beta, MAD-CT-2, or Fos-related antigen 1. Such tumor antigens have been ranked based on criteria such as a) therapeutic function, b) immunogenicity, c) role of the antigen in oncogenicity, d) specificity, expression level and percent of antigen-positive cells, e) stem cell expression, f) number of patients with antigen-positive cancers, g) number of antigenic epitopes and h) cellular location of antigen expression (see Cheever, M. A. et al., Clincal Cancer Research, Sep. 1, 2009, 15(17):5323-5337). In some embodiments, the tumor antigen is one or more of survivin, Her-2, EFGRvIII, PSA, PAP or PMSA.

In aspects of the invention, an antigen is an allergen. An allergen refers to a substance (antigen) that can induce an allergic or asthmatic response in a susceptible subject. The list of allergens is enormous and can include pollens, insect venoms, animal dander dust, fungal spores and drugs (e.g. penicillin). Examples of natural, animal and plant allergens include but are not limited to proteins specific to the following genuses: *Agropyron* (e.g. *Agropyron repens*); *Agrostis* (e.g. *Agrostis alba*); Alder, *Alnus* (*Alnus gultinoasa*); *Alternaria* (*Alternaria alternata*); *Ambrosia* (*Ambrosia artemiisfolia; Anthoxanthum* (e.g. *Anthoxanthum odoratum*); *Apis* (e.g. *Apis multiflorum*); *Arrhenatherum* (e.g. *Arrhenatherum elatius*); *Artemisia* (*Artemisia vulgaris*); *Avena* (e.g. *Avena sativa*); *Betula* (*Betula verrucosa*); *Blat-* tella (e.g. *Blattella germanica*); *Bromus* (e.g. *Bromus inermis*); *Canine* (*Canis familfaris*); *Chamaecyparis* (e.g. *Chamaecyparis obtuse*); *Cryptomeria* (*Cryptomeria japonica*); *Cupressus* (e.g. *Cupressus sempervirens*, *Cupressus arizonica* and *Cupressus macrocarpa*); *Dactylis* (e.g. *Dactylis glomerate*); *Dermatophagoides* (e.g. *Dermatophagoides farinae*); *Fells* (*Fells domesticus*); *Festuca* (e.g. *Festuca elation*); *Holcus* (e.g. *Holcus lanatus*); *Juniperus* (e.g. *Juniperus sabinoides, Juniperus virginiana, Juniperus communis* and *Juniperus ashei*); *Lolium* (e.g. *Lolium perenne* or *Lolium multiflorum*); *Olea* (*Olea europa*); *Parietaria* (e.g. *Parietaria officinalis* or *Parietaria Judaica*); *Paspalum* (e.g. *Paspalum notatum*); *Periplaneta* (e.g. *Periplaneta americana*); *Phalaris* (e.g. *Phalaris arundinacea*); *Phleum* (e.g. *Phleum pretense*); *Plantago* (e.g. *Plantago lanceolate*); *Poa* (e.g. *Poa pratensis* or *Poa compressa*); *Quercus* (*Quercus alba*); *Secale* (e.g. *Secale cereale*); *Sorghum* (e.g. *Sorghum halepensis*); *Thuya* (e.g. *Thuya orientalis*); and *Triticum* (e.g. *Triticum aestivum*), and combinations thereof.

In aspects of the invention, an antigen is an addictive substance. An addictive substance is any chemical or biological substance, including synthetic or artificial substances, that cause a subject to develop an addiction to that substance. In some aspects, an addictive substance is nicotine or cocaine. In some embodiments, the antigen in a vaccine against a nicotine addiction is nicotine or a nicotine-like hapten conjugated to a carrier. In some embodiments, the carrier to which nicotine or nicotine-like hapten is conjugated is diphtheria toxoid.

In aspects of the invention, an antigen or a hapten is conjugated to a carrier protein. In some aspects, the carrier protein is a bacterial toxoid or derivative, *Pseudomonas* exotoxin, KLH or a virus-like particle. In some aspects, a bacterial toxoid is diphtheria toxoid or a derivative thereof. In some aspects, a bacterial toxoid is CRM197. In some aspects, the virus-like particle is HBsAg, HBcAg, *E. coli* bacteriophage Qβ, Norwalk virus or influenza HA.

Aspects of the invention relate to vaccines having cholesterol. Cholesterol is a white crystalline substance with a chemical formula of $C_{27}H_{45}OH$. It is a cyclic hydrocarbon alcohol which is classified as a lipid. A lipid is any group of organic compounds, including, but not limited to, the fats, oils, waxes, sterols and triglycerides, that are insoluble in water but are soluble in nonpolar organic solvents, are oily to the touch and together with carbohydrates and proteins are the principal structural material of living cells. Cholesterol is insoluble in water but is soluble in a number of organic solvents.

In aspects of the invention, sterol refers to compounds in animals which are biologically produced from perpenoid precursors. They comprise a steroid ring structure, having a hydroxyl (OH) group. In some aspects, the hydroxyl group may be attached to carbon-3. The hydrocarbon chain of the fatty-acid substituent varies in length. In some aspects, the hydrocarbon chain may be from 16 to 20 carbon atoms. In some aspects, the hydrocarbon chain may be saturated or unsaturated. Sterols can contain one or more double bonds in the ring structure and may also include a variety of substituents attached to the rings. Sterols and their fatty-acid esters may be water insoluble. Fatty-acid esters relate to any of a class of organic compounds corresponding to inorganic salts, which are formed from a condensation reaction in which a molecule of an organic acid unites with a molecule of alcohol with the elimination of a molecule of water. In some aspects, sterols refers to synthetic sterols. In some aspects, synthetic steroids includes, but is not limited to, glucocorticoids (for example, prednisone, dexamethasone, triamcinolone), mineralocorticoid (for example, fludrocortisones), vitamin D (for example, dihydrotachysterol), androgens (for example, oxandrolone, nandrolone, anabolic steroids), estrogens (for example, diethylstilbestrol) and progestins (for example, norethindrone, medroxyprogesterone acetate). In some aspects, a cholate may be used, for example sodium deoxycholate.

In aspects of the invention, sterols include, but are not limited to, natural steroids such as, β-sitosterol, stigmasterol, ergosterol, ergocalciferol, and cholesterol. Such sterols may be purchased commercially. Cholesterol, for example, is disclosed in the Merck Index, $12^{th}$ Ed., p. 369.

In aspects of the invention, sterols may be used as an adjuvant. In some aspects, the amount of sterol may be about 1 µg to about 5,000 µg per vaccine dose. In some aspects, the amount of sterol may be about 1 µg to about 4,000 µg per vaccine dose, about 1 µg to about 3,000 µg per vaccine dose, about 1 µg to about 2,000 µg per vaccine dose, or about 1 µg to about 1,000 µg per vaccine dose. In some aspects, the amount of sterol may be about 5 µg to about 750 µg per vaccine dose, about 5 µg to about 500 µg per vaccine dose, about 5 µg to about 250 µg per vaccine dose, about 5 µg to about 100 µg per vaccine dose, about 15 µg to about 100 µg per vaccine dose, or about 30 µg to about 75 µg per vaccine dose.

In aspects of the invention, a vaccine has one or more antigens and cholesterol. In some aspects, the amount of cholesterol relative to the amount of antigen is about 0.1 to about 50 fold greater by weight. In some aspects, the amount of cholesterol is about 1 to about 10 fold greater by weight than the antigen. In some aspects, the amount of cholesterol is equal in weight to the antigen.

In aspects of the invention, a vaccine has one or more antigens and one or more immune modulatory molecules and cholesterol. In some aspects, a vaccine further includes a pharmaceutical carrier.

In aspects of the invention, "in conjunction" or "in conjunction with" refers to an admixture, a combination or being in close proximity to one or more antigens, and one or more antigens and one or more immune modulatory molecules. In aspects, the one or more antigens and/or the one or more immune modulatory molecules may be attached to cholesterol by a physical means via one or more linkers. A linker includes, but is not limited to, direct or indirect linkers. In aspects, the one or more antigens and/or one or more immune modulatory molecules and cholesterol may be encapsulated together.

In aspects of the invention, one or more antigens may be admixed with one or more immune modulatory molecules. In aspects, one or more antigens may be admixed with cholesterol. In aspects, one or more immune modulatory molecules may be admixed with cholesterol. In aspects, one or more immune modulatory molecules may be admixed with antigen and cholesterol. In aspects, one or more immune modulatory molecules may be admixed with cholesterol and one or more antigens may be separate. In aspects, one or more antigens may be admixed with cholesterol and one or more immune modulatory molecules may be separate. In aspects, one or more antigens and/or one or more immune modulatory molecules may be in conjunction with cholesterol.

In aspects of the invention, the amount of cholesterol relative to the amount of antigen is greater than the amount of antigen. In some aspects, the amount of cholesterol relative to the amount of antigen is about 0.1 to 50 fold greater by weight than the antigen. In aspects, the amount of cholesterol relative to the amount of antigen is about 10 to about 50 fold, about 20 to about 40 fold, about 30 to about 35 fold greater by weight than the antigen. In aspects, the amount of cholesterol relative to the amount of antigen is about 1 to about 10 fold greater by weight than the antigen. In aspects, the amount of cholesterol relative to the amount of antigen is equal in weight to the antigen. In aspects, the antigen may be one or more antigens and the weight of the antigen is the total weight of the one or more antigens.

In aspects of the invention, an immune modulatory molecule (one or more immune modulatory molecules) is a molecule that modulates immune cells in a subject. This effect may be mediated directly, for example, through a receptor, or indirectly, for example, through cytokines or chemokines released from another immune cell that is modulated directly. An induction of an immune response refers to any increase in number or activity of an immune cell, or an increase in expression or absolute levels of an immune factor, such as a cytokine. Immune cells include, but are not limited to, NK cells, CD4+ T lymphocytes, CD8+ T lymphocytes, B cells, dendritic cells, macrophage and other antigen-presenting cells. Cytokines include, but are not limited to, interleukins, TNF-α, IFN-α,β and γ. In aspects, an immune modulator is a molecule which when used with an antigen enhances antigen specific humoral (for example, antibody) and or cellular (for example, T cell) immune responses.

In some aspects, an immune modulatory molecule is a TLR agonist, an antimicrobial peptide, a cytokine, a chemokine, a NOD ligand or an oligonucleotide. In some aspects, a TLR agonist is an oligoribonucleotide (ORN) or a small molecule that activates TLR 7 and/or TLR 8. In some aspects, a TLR agonist is an oligodeoxynucleotide (ODN) that activates through TLR 9. In some aspects, a TLR 9 agonist is an ODN containing unmethylated CpG motifs, a B-Class oligodeoxynucleotide, a C-Class oligodeoxynucleotide or a P-Class oligodeoxynucleotide. In some aspects, a TLR 9 agonist is IMO-2055, IMO-2125 or IMO-2134 (QAX935). In other aspects, a TLR agonist is a poly I:C that activates TLR 3. In some aspects, the poly I:C is ODN1a having the sequence 5'-ICI CIC ICI CIC ICI CIC ICI CIC IC-3' (SEQ ID NO:16).

In aspects of the invention, an oligonucleotide can encompass various chemical modifications and substitutions, in comparison to natural RNA and DNA, involving a phosphodiester internucleoside bridge, a β-D-ribose unit and/or a natural nucleoside base (adenine, guanine, cytosine, thymine, uracil). Examples of chemical modifications are known to the skilled person and are described, for example, in Uhlmann E et al. (1990) *Chem Rev* 90:543; "Protocols for Oligonucleotides and Analogs" Synthesis and Properties & Synthesis and Analytical Techniques, S. Agrawal, Ed, Humana Press, Totowa, USA 1993; Crooke S T et al. (1996) *Annu Rev Pharmacol Toxicol* 36:107-129; and Hunziker J et al. (1995) *Mod Synth Methods* 7:331-417. In some aspects, an oligonucleotide may have one or more modifications, wherein each modification is located at a particular phosphodiester internucleoside bridge and/or at a particular β-D-ribose unit and/or at a particular natural nucleoside base position in comparison to an oligonucleotide of the same sequence which is composed of natural DNA or RNA.

In some aspects, the oligonucleotides may comprise one or more modifications and wherein each modification is independently selected from:
a) the replacement of a phosphodiester internucleoside bridge located at the 3' and/or the 5' end of a nucleoside by a modified internucleoside bridge,
b) the replacement of phosphodiester bridge located at the 3' and/or the 5' end of a nucleoside by a dephospho bridge,
c) the replacement of a sugar phosphate unit from the sugar phosphate backbone by another unit,
d) the replacement of a β-D-ribose unit by a modified sugar unit, and
e) the replacement of a natural nucleoside base by a modified nucleoside base.

In aspects of the invention, the oligonucleotides may include modified internucleotide linkages, such as those described in a) or b) above. These modified linkages may be partially resistant to degradation (e.g., are stabilized). A "stabilized oligonucleotide molecule" is an oligonucleotide that is relatively resistant to in vivo degradation (e.g. via an exo- or endo-nuclease) resulting from such modifications. Oligonucleotides having phosphorothioate linkages, in some aspects, may provide maximal activity and protect the oligonucleotide from degradation by intracellular exo- and endo-nucleases.

A phosphodiester internucleoside bridge located at the 3' and/or the 5' end of a nucleoside can be replaced by a modified internucleoside bridge, wherein the modified internucleoside bridge is, for example, selected from phosphorothioate, phosphorodithioate, $NR^1R^2$-phosphoramidate, boranophosphate, α-hydroxybenzyl phosphonate, phosphate-$(C_1-C_{21})$—O-alkyl ester, phosphate-$[(C_6-C_{12})$aryl-$(C_1-C_{21})$—O-alkyl]ester, $(C_1-C_8)$alkylphosphonate and/or $(C_6-C_{12})$arylphosphonate bridges, $(C_7-C_{12})$-α-hydroxymethyl-aryl (e.g., disclosed in WO 95/01363), wherein $(C_6-C_{12})$aryl, $(C_6-C_{20})$aryl and $(C_6-C_{14})$aryl are optionally substituted by halogen, alkyl, alkoxy, nitro, cyano, and where $R^1$ and $R^2$ are, independently of each other, hydrogen, $(C_1-C_{18})$-alkyl, $(C_6-C_{20})$-aryl, $(C_6-C_{14})$-aryl-$(C_1-C_8)$-alkyl, preferably hydrogen, $(C_1-C_8)$-alkyl, preferably $(C_1-C_4)$-alkyl and/or methoxyethyl, or $R^1$ and $R^2$ form, together with the nitrogen atom carrying them, a 5-6-membered heterocyclic ring which can additionally contain a further heteroatom from the group O, S and N.

The replacement of a phosphodiester bridge located at the 3' and/or the 5' end of a nucleoside by a dephospho bridge (dephospho bridges are described, for example, in Uhlmann E and Peyman A in "Methods in Molecular Biology", Vol. 20, "Protocols for Oligonucleotides and Analogs", S. Agrawal, Ed., Humana Press, Totowa 1993, Chapter 16, pp. 355 ff), wherein a dephospho bridge is for example selected from the dephospho bridges formacetal, 34-hioformacetal, methylhydroxylamine, oxime, methylenedimethyl-hydrazo, dimethylenesulfone and/or silyl groups.

A sugar phosphate unit (i.e., a β-D-ribose and phosphodiester internucleoside bridge together forming a sugar phosphate unit) from the sugar phosphate backbone (i.e., a sugar phosphate backbone is composed of sugar phosphate units) can be replaced by another unit, wherein the other unit is, for example, suitable to build up a "morpholino-derivative" oligomer (as described, for example, in Stirchak E P et al. (1989) *Nucleic Acids Res* 17:6129-41), that is, e.g., the replacement by a morpholino-derivative unit; or to build up a polyamide nucleic acid ("PNA": as described for example, in Nielsen P E et al. (1994) *Bioconjug Chem* 5:3-7), that is, e.g., the replacement by a PNA backbone unit, e.g., by 2-aminoethylglycine. The oligonucleotide may have other carbohydrate backbone modifications and replacements, such as peptide nucleic acids with phosphate groups (PHONA), locked nucleic acids (LNA), and oligonucleotides having backbone sections with alkyl linkers or amino linkers. The alkyl linker may be branched or unbranched, substituted or unsubstituted, and chirally pure or a racemic mixture.

A β-ribose unit or a β-D-2'-deoxyribose unit can be replaced by a modified sugar unit, wherein the modified sugar unit is, for example, selected from β-D-ribose, α-D-2'-deoxyribose, L-2'-deoxyribose, 2'-F-2'-deoxyribose, 2-F-arabinose, 2'-O—($C_1$-$C_6$)alkyl-ribose, preferably 2'-O—($C_1$-$C_6$)alkyl-ribose is 2'-O-methylribose, 2'-O—($C_2$-$C_6$)alkenyl-ribose, 2'-[O—($C_1$-$C_6$)alkyl-O—($C_1$-$C_6$)alkyl]-ribose, 2'-$NH_2$-2'-deoxyribose, β-D-xylo-furanose, α-arabinofuranose, 2,4-dideoxy-β-D-erythro-hexo-pyranose, and carbocyclic (described, for example, in Froehler J (1992) *Am Chem Soc* 114:8320) and/or open-chain sugar analogs (described, for example, in Vandendriessche et al. (1993) *Tetrahedron* 49:7223) and/or bicyclosugar analogs (described, for example, in Tarkov M et al. (1993) *Helv Chim Acta* 76:481).

In some aspects, the sugar is 2'-O-methylribose, for one or both nucleotides linked by a phosphodiester or phosphodiester-like internucleoside linkage.

Nucleic acids also include, but are not limited to, substituted purines and pyrimidines such as C-5 propyne pyrimidine and 7-deaza-7-substituted purine modified bases. Wagner R W et al. (1996) Nat Biotechnol 14:840-4. Purines and pyrimidines include, but are not limited to, adenine, cytosine, guanine, and thymine, and other naturally and non-naturally occurring nucleobases, substituted and unsubstituted aromatic moieties.

A modified base is any base which is chemically distinct from the naturally occurring bases typically found in DNA and RNA such as T, C, G, A, and U, but which share basic chemical structures with these naturally occurring bases. The modified nucleoside base may be, for example, selected from hypoxanthine, uracil, dihydrouracil, pseudouracil, 2-thiouracil, 4-thiouracil, 5-aminouracil, 5-($C_1$-$C_6$)-alkyluracil, 5-($C_2$-$C_6$)-alkenyluracil, 5-($C_2$-$C_6$)-alkynyluracil, 5-(hydroxymethyl)uracil, 5-chlorouracil, 5-fluorouracil, 5-bromouracil, 5-hydroxycytosine, 5-($C_1$-$C_6$)-alkylcytosine, 5-($C_2$-$C_6$)-alkenylcytosine, 5-($C_2$-$C_6$)-alkynylcytosine, 5-chlorocytosine, 5-fluorocytosine, 5-bromocytosine, $N^2$-dimethylguanine, 2,4-diamino-purine, 8-azapurine, a substituted 7-deazapurine, preferably 7-deaza-7-substituted and/or 7-deaza-8-substituted purine, 5-hydroxymethylcytosine, N4-alkylcytosine, e.g., N4-ethylcytosine, 5-hydroxydeoxycytidine, 5-hydroxymethyldeoxycytidine, N4-alkyldeoxycytidine, e.g., N4-ethyldeoxycytidine, 6-thiodeoxyguanosine, and deoxyribonucleosides of nitropyrrole, C5-propynylpyrimidine, and diaminopurine e.g., 2,6-diaminopurine, inosine, 5-methylcytosine, 2-aminopurine, 2-amino-6-chloropurine, hypoxanthine or other modifications of a natural nucleoside bases. This list is meant to be exemplary and is not to be interpreted to be limiting.

In aspects of the invention, for some formulas described herein a set of modified bases is defined. For instance, the letter Y is used to refer to a nucleotide containing a cytosine or a modified cytosine. A modified cytosine is a naturally occurring or non-naturally occurring pyrimidine base analog of cytosine which can replace this base without impairing the immunostimulatory or immune modulatory activity of the oligonucleotide. Modified cytosines include but are not limited to 5-substituted cytosines (e.g. 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g. N4-ethyl-cytosine), 5-aza-cytosine, 2-mercapto-cytosine, isocytosine, pseudo-isocytosine, cytosine analogs with condensed ring systems (e.g. N,N'-propylene cytosine or phenoxazine), and uracil and its derivatives (e.g. 5-fluoro-uracil, 5-bromo-uracil, 5-bromovinyl-uracil, 4-thio-uracil, 5-hydroxy-uracil, 5-propynyl-uracil). In some aspects, cytosines include 5-methyl-cytosine, 5-fluoro-cytosine, 5-hydroxy-cytosine, 5-hydroxymethyl-cytosine, and N4-ethyl-cytosine. In some aspects, the cytosine base is substituted by a universal base (e.g. 3-nitropyrrole, P-base), an aromatic ring system (e.g. fluorobenzene or difluorobenzene) or a hydrogen atom (dSpacer).

The letter R is used to refer to guanine or a modified guanine base. A modified guanine is a naturally occurring or non-naturally occurring purine base analog of guanine which can replace this base without impairing the immunostimulatory or immune modulatory activity of the oligonucleotide. Modified guanines include but are not limited to 7-deazaguanine, 7-deaza-7-substituted guanine (such as, 7-deaza-7-(C2-C6)alkynylguanine), 7-deaza-8-substituted guanine, hypoxanthine, N2-substituted guanines (e.g. N2-methyl-guanine), 5-amino-3-methyl-3H,6H-thiazolo[4,5-d]pyrimidine-2,7-dione, 2,6-diaminopurine, 2-aminopurine, purine, indole, adenine, substituted adenines (e.g. N6-methyl-adenine, 8-oxo-adenine) 8-substituted guanine (e.g. 8-hydroxyguanine and 8-bromoguanine), and 6-thioguanine. In some aspects, the guanine base is substituted by a universal base (e.g. 4-methyl-indole, 5-nitro-indole, and K-base), an aromatic ring system (e.g. benzimidazole or dichloro-benzimidazole, 1-methyl-1H-[1,2,4]triazole-3-carboxylic acid amide) or a hydrogen atom (dSpacer).

In some aspects, other base modifications are also contemplated. For example, the terminal T residues at either end of an oligonucleotide may be replaced by deoxyuridine (U), the G of one or more CpG motifs may be replaced with deoxyinosine (I), and the modification of G residues as 7-deaza deoxyguanosine. In some aspects, the 5' terminal T of an oligonucleotide may include a halogen substitution. In some aspects, the halogen substitution is ethyl-uridine, bromo-uridine, chloro-uridine or iodo-uridine.

In aspects of the instant invention, the oligonucleotides can be synthesized de novo using any of a number of procedures well known in the art. For example, the b-cyanoethyl phosphoramidite method (Beaucage, S. L., and Caruthers, M. H., *Tet. Let.* 22:1859, 1981); nucleoside H-phosphonate method (Garegg et al., *Tet. Let.* 27:4051-4054, 1986; Froehler at al., *Nucl. Acid. Res.* 14:5399-5407, 1986; Garegg at al., *Tet. Let.* 27:4055-4058, 1986, Gaffney at al., *Tet. Let.* 29:2619-2622, 1988). These chemistries can be performed by a variety of automated nucleic acid synthesizers available in the market. These oligonucleotides are referred to as synthetic oligonucleotides. An isolated oligonucleotide generally refers to an oligonucleotide which is separated from components which it is normally associated with in nature. As an example, an isolated oligonucleotide may be one which is separated from a cell, from a nucleus, from mitochondria or from chromatin.

In some aspects of the invention, the internucleotide linkages in the oligonucleotide may be a non-stabilized or stabilized linkage (against nucleases), a phosphodiester (non stabilized), a phosphorothioate (stabilized) or another charged backbone, or a phosphodiester linkage. In some aspects, if the internucleotide linkage at Y—R is a phosphorothioate, the chirality of this linkage may be random, or is preferably a phosphorothioate linkage of Rp configuration.

In aspects of the invention, modified backbones, such as phosphorothioates, may be synthesized using automated techniques employing either phosphoramidate or H-phosphonate chemistries. Aryl- and alkyl-phosphonates can be made, e.g., as described in U.S. Pat. No. 4,469,863; and alkylphosphotriesters (in which the charged oxygen moiety is alkylated as described in U.S. Pat. No. 5,023,243 and European Patent No. 0,092,574) can be prepared by automated solid phase synthesis using commercially available reagents. Methods for making other DNA backbone modifications and substitutions have been described (e.g., Uhlmann, E. and Peyman, A., Chem. Rev. 90:544, 1990; Goodchild, J., Bioconjugate Chem. 1:165, 1990). The symbol * refers to the presence of a stabilized internucleotide linkage and _ refers to the presence of a phosphodiester linkage. In aspects, the one or more immune modulatory molecules may each independently, have a wholly native phosphodiester backbone.

In aspects of the invention, the one or more immune modulatory molecules are oligonucleotides which include at least one unmethylated CpG dinucleotide. An oligonucleotide containing at least one unmethylated CpG dinucleotide is a nucleic acid molecule which contains an unmethylated cytosine-guanine dinucleotide sequence (i.e., "CpG DNA" or DNA containing a 5' cytosine followed by 3' guanine and linked by a phosphate bond) and activates the immune system. The entire CpG oligonucleotide can be unmethylated or portions may be unmethylated but at least the C of the 5' CG 3' must be unmethylated. CpG The terms CpG oligonucleotide or CpG nucleic acid as used herein refer to an immunostimulatory CpG oligonucleotide or a nucleic acid unless otherwise indicated.

In aspects of the invention, immune modulatory molecules include, but are not limited to, oligonucleotides that are A-Class, B-Class, C-Class, T-Class, P-Class or any Class with an E modification.

A-Class oligonucleotides are potent for inducing IFN-α and NK cell activation but is relatively weak at stimulating B cells. The A-Class oligonucleotides typically have stabilized poly-G sequences at 5' and 3' ends and a palindromic phosphodiester CpG dinucleotide-containing sequence of at least 6 nucleotides and form multimeric structures. A-Class oligonucleotides have been described in U.S. Pat. No. 6,949,520, issued Sep. 27, 2005 and published PCT application no. PCT/US00/26527 (WO 01/22990), published on Apr. 5, 2001 The A-Class oligonucleotides do not necessarily contain a hexamer palindrome GACGTC, AGCGCT, or AACGTT, described by Yamamoto and colleagues. Yamamoto S et al. *J Immunol* 148:4072-6 (1992). In aspects, an "A-Class" CpG oligonucleotide has the following nucleic acid sequence: 5' GGGGACGACGTCGTGGGGGGG 3' (SEQ ID NO:17). In aspects, an A-Class oligonucleotide includes, but is not limited to, 5'G*G*G_G_A_C_G_A_C_G_T_C_G_T_G_G*G*G*G*G 3' (SEQ ID NO:18); wherein * refers to a phosphorothioate bond _ and refers to a phosphodiester bond.

B-Class oligonucleotides are potent at activating B cells but are relatively weak in inducing IFN-α and NK cell activation. The B-Class oligonucleotides are monomeric and may be fully stabilized with a wholly phosphorothioate backbone. B-Class oligonucleotides may also have some native phosphodiester linkages, for example, between the C and G of the CpG, in which case they are referred to as semi-soft. In aspects, a B class CpG oligonucleotide may be represented by at least the formula: 5' $X_1X_2CGX_3X_4$ 3', wherein X1, X2, X3, and X4 are nucleotides. In aspects, $X_2$ is adenine, guanine, or thymine. In aspects, $X_3$ is cytosine, adenine, or thymine. In aspects, a B class CpG oligonucleotide may be represented by at least the formula: 5' $N_1X_1X_2CGX_3X_4N_2$ 3', wherein $X_1$, $X_2$, $X_3$, and $X_4$ are nucleotides and N is any nucleotide and $N_1$ and $N_2$ are nucleic acid sequences composed of from about 0-25 N's each. In aspects, $X_1X_2$ is a dinucleotide selected from the group consisting of GpT, GpG, GpA, ApA, ApT, ApG, CpT, CpA, CpG, TpA, TpT and TpG; and $X_3X_4$ is a dinucleotide selected from the group consisting of TpT, ApT, TpG, ApG, CpG, TpC, ApC, CpC, TpA, ApA and CpA. In some aspects, $X_1X_2$ is GpA or GpT and $X_3X_4$ is TpT. in aspects, $X_1$ or $X_2$ or both are purines and $X_3$ or $X_4$ or both are pyrimidines or $X_1X_2$ is GpA and $X_3$ or $X_4$ or both are pyrimidines. In some aspects, $X_1X_2$ is a dinucleotide selected from the group consisting of TpA, ApA, ApC, ApG and GpG. in some aspects, $X_3X_4$ is a dinucleotide selected from the group consisting of TpT, TpA, TpG, ApA, ApG, GpA and CpA. $X_1X_2$, in some aspects, is a dinucleotide selected from the group consisting of TpT, TpG, ApT, GpC, CpC, CpT, TpC, GpT and CpG; $X_3$ is a nucleotide selected from the group consisting of A and T, and $X_4$ is a nucleotide, but when $X_1X_2$ is TpC, GpT or CpG, $X_3X_4$ is not TpC, ApT or ApC. In aspects, the CpG oligonucleotide has the sequence 5' $TCN_1TX_1X_2CGX_3X_4$ 3'. The CpG oligonucleotides of the invention, may include, for example, $X_1X_2$ selected from the group consisting of GpT, GpG, GpA and ApA and $X_3X_4$ selected from the group consisting of TpT, CpT and TpC. B-Class oligonucleotides have been described in U.S. Pat. Nos. 6,194,388 B1 and 6,239,116 B1, issued on Feb. 27, 2001 and May 29, 2001 respectively, and in published PCT application no. WO/1996/002555, published on Feb. 1, 1996 and published PCT application no. WO/1998/018810, published on May 7, 1998. In some aspects, a B-Class oligonucleotide is

CPG 7909
(SEQ ID NO: 1)
5' TCGTCGTTTTGTCGTTTTGTCGTT 3',

CpG 24555
(SEQ ID NO: 2)
5' TCGTCGTTTTTCGGTGCTTTT 3',

CPG 10104
(SEQ ID NO: 3)
TCGTCGTTTCGTCGTTTTGTCGTT, (SEQ ID NO: 19)
5' TCGTCGTTTTGTCGTTTTGTCGTT 3', (SEQ ID NO: 20)
5' TCGTCGTTTTGTCGTTTTTTTCGA 3', (SEQ ID NO: 21)
5' T*C*G*T*C*G*T*T*T*T*T*C*G*G*T*G*C*T*T*T*T 3', (SEQ ID NO: 22)
5' T*C*G*T*C*G*T*T*T*T*T*C*G*G*T*C*G*T*T*T*T 3', (SEQ ID NO: 23)
5' T*C*G*T*C*G*T*T*T*T*G*T*C*G*T*T*T*T*G*T*C*G*T*T 3', (SEQ ID NO: 24)
5' T*C*G*T*C*G*T*T*T*C*G*T*C*G*T*T*T*T*G*T*C*G*T*T 3',
or (SEQ ID NO: 25)
5' T*C*G*T*C*G*T*T*T*T*G*T*C*G*T*T*T*T*T*C*G*A 3' wherein * refers to a phosphorothioate bond.

C-Class oligonucleotides have both a traditional "stimulatory" CpG sequence and a "GC-rich" or "B-cell neutralizing" motif. C-Class CpG oligonucleotides have properties intermediate to A- and B-Classes so activate B cells and NK cells and induce IFN-α (Krieg A M et al. (1995) *Nature* 374:546-9; Ballas Z K et al. (1996) *J Immunol* 157:1840-5; Yamamoto S et al. (1992) *J Immunol* 148:4072-6). The C-Class oligonucleotides, contain a single palindrome such that they can form secondary structures such as stem-loops or tertiary structures such as dimmers. The backbone of C-Class oligonucleotides may have a fully stabilized, chimeric or semi-soft backbone. C-Class oligonucleotides include a B-Class-type sequence and a GC-rich palindrome or near-palindrome. This Class has been described in US published application no. 20030148976, published on Aug. 7, 2003 and in published PCT application no. WO2008/068638, published on Jun. 12, 2008. In some aspects, a C-Class oligonucleotide is CPG 10101 5' TCGTCGTTTTCGGCGGCCGCCG 3' (SEQ ID NO:4), CPG 10109 5' TCGTC-GTTTTAC-GGCGCC-GTCCCG 3' (SEQ ID NO:5 where dashes represent semi-soft phosphodiester linkages), CpG 23407 5' TC-GTCGTTTTCG-GCGCGCGCCGT 3' (SEQ ID NO:6 where the dash represents a semi-soft phosphodiester linkage),

```
                                    (SEQ ID NO: 26)
5' TCGCGTCGTTCGGCGCGCGCCG 3', (SEQ ID NO: 27)
5' TCGTCGACGTTCGGCGCGCGCCG 3', (SEQ ID NO: 28)
5' TCGGACGTTCGGCGCGCGCCG 3', (SEQ ID NO: 29)
5' TCGGACGTTCGGCGCGCCG 3', (SEQ ID NO: 30)
5' TCGCGTCGTTCGGCGCGCCG 3', (SEQ ID NO: 31)
5' TCGACGTTCGGCGCGCGCCG 3', (SEQ ID NO: 32)
5' TCGACGTTCGGCGCGCCG 3', (SEQ ID NO: 33)
5' TCGCGTCGTTCGGCGCCG 3', (SEQ ID NO: 34)
5' TCGCGACGTTCGGCGCGCGCCG 3',
or
                                    (SEQ ID NO: 35)
5' TCGTCGTTTTCGGCGCGCGCCG 3'.
```

In aspects, a C-Class CpG oligonucleotide is

```
                                    (SEQ ID NO: 38)
5' T*C_G*C_G*T*C_G*T*T*C_G*G*C*G*C_G*C*G*C*C*G 3', (SEQ ID NO: 39)
5' T*C_G*T*C_G*A*C_G*T*T*C_G*G*C*G*C_G*C*G*C*C*G
3', (SEQ ID NO: 40)
5' T*C_G*G*A*C_G*T*T*C_G*G*C*G*C_G*C*G*C*C*G 3', (SEQ ID NO: 41)
5' T*C_G*G*A*C_G*T*T*C_G*G*C*G*C*G*C*C*G 3', (SEQ ID NO: 42)
5' T*C_G*C_G*T*C_G*T*T*C_G*G*C*G*C*G*C*C*G 3', (SEQ ID NO: 43)
5' T*C_G*A*C_G*T*T*C_G*G*C*G*C_G*C*G*C*C*G 3', (SEQ ID NO: 44)
5' T*C_G*A*C_G*T*T*C_G*G*C*G*C*G*C*C*G 3', (SEQ ID NO: 45)
5' T*C_G*C_G*T*C_G*T*T*C_G*G*C*G*C*C*G 3', (SEQ ID NO: 46)
5' T*C_G*C_G*A*C_G*T*T*C_G*G*C*G*C_G*C*G*C*C*G
3', (SEQ ID NO: 47)
5' T*C*G*T*C*G*T*T*T*T*C*G*G*C*G*C*G*C*G*C*C*G
3', (SEQ ID NO: 48)
5' T*C*G*T*C*G*T*T*T*T*C*G*G*C*G*C*G*C*G*C*C*G 3', (SEQ ID NO: 49)
5' T*C*G*T*C_G*T*T*T*T*A*C_G*G*C*G*C*C_G*T*G*C*C*G
3'
or
                                    (SEQ ID NO: 50)
5' T*C G*T*C*G*T*T*T*T*C*G*G*C*G*C*G*C*G*C*C*G*T
3'
wherein * refers to a phosphorothioate
bond and _ refers to a phosphodiester bond.
```

In any of these sequences, an ethyl-uridine or a halogen may substitute for the 5' T; examples of halogen substitutions include, but are not limited to, bromo-uridine or iodo-uridine substitutions.

The P-Class oligonucleotides have the ability in some instances to induce much higher levels of IFN-α secretion than the C-Class oligonucleotides. The P-Class oligonucleotides have the ability to spontaneously self-assemble into concatamers either in vitro and/or in vivo. P-Class oligonucleotides are further disclosed in published PCT application no. WO2008/068638, published on Jun. 12, 2008. In some aspects, a P-Class oligonucleotide is CpG 21798
```
                                    (SEQ ID NO: 7)
5' T*C-G*T*C-G*A*C-G*A*T*C-G*G*C*G*C-G*C*G*C*C*G
3',
```

CpG 23430
```
                                    (SEQ ID NO: 8)
5' T*C-G*A*C*G*T*C*G*A*T*C*G*G*C*G*C*G*C*G*C*C*G
3',
```

CpG 24558
```
                                    (SEQ ID NO: 9)
5' T*C*G*A*C*G*T*C*G*A*T*C*G*G*C*G*C*G*C*G*C*C*G*T
3',
```

CpG 23871
```
                                    (SEQ ID NO: 10)
5' JU*C-G*A*C*G*T*C*G*A*T*C*G*G*C*G*C*G*C*G*C*C*G
3',
```

-continued

CpG 23873

(SEQ ID NO: 11)
5' JU*C-G*A*C*G*T*C*G*A*T*C*G*G*C*G*C*G*C*
G*T 3',

CpG 23874

(SEQ ID NO: 12)
5' JU*C*G*A*C*G*T*C*G*A*T*C*G*G*C*G*C*G*C*C*
G*T 3',

CpG 23875

(SEQ ID NO: 13)
5' EU*C-G*A*C*G*T*C*G*A*T*C*G*G*C*G*C*G*C*C*G
3',

CpG 23877

(SEQ ID NO: 14)
5' JU*C-G*T*C*G*A*C*G*A*T*C*G*G*C*G*G*C*C*G*C*C*
G*T 3',

CpG 23878

(SEQ ID NO: 15)
5' JU*C*G*T*C*G*A*C*G*A*T*C*G*G*C*G*G*C*C*G*C*C*
G*T 3'
or (SEQ ID NO: 37)
5' T*C_G*T*C_G*A*C_G*A*T*C_G*G*C*G*C_G*C*G*C*C*G
3'.

The T-Class oligonucleotides induce secretion of lower levels of IFN-alpha and IFN-related cytokines and chemokines than B-Class or C-Class oligonucleotides, while retaining the ability to induce levels of IL-10 similar to B-Class oligonucleotides. T-Class oligonucleotides are further disclosed in published PCT application WO2008/068638, published on Jun. 12, 2008.

E modifications can be made on any class of CpG oligonucleotides. These are oligonucleotides with lipophilic substituted nucleotide analogs outside the CpG motif and have enhanced ability to stimulate interferon-α (IFN-α) production and induce TLR9 activation. E modified oligonucleotides are further disclosed in published PCT application WO2008/068638, published on Jun. 12, 2008.

In aspects of the invention, the one or more immune modulatory molecules are in an effective amount to induce or enhance an antigen-specific immune response. In some aspects, the antigen-specific immune response enhanced is a Th1 immune response. In some aspects, the Th1 immune response results in the antigen-specific induction of IFN-γ, or the induction of poly-functional T cells that secrete two or more cytokines. In some aspects, the cytokines include, but are not limited to, IL-2 and IFN-γ or IFN-γ, TNF-α and IL-2.

In aspects of the invention, the amount of immune modulatory molecule is from about 1 μg to about 5 mg per vaccine dose. In some aspects, the amount of immune modulatory molecules is from about 1 μg to about 4 mg per vaccine dose, about 1 μg to about 3 mg per vaccine dose, about 1 μg to about 2 mg per vaccine dose, or about 1 μg to about 1 mg per vaccine dose. In some aspects, the amount of immune modulatory molecules is from about 10 μg to about 750 μg per vaccine dose, about 10 μg to about 500 μg per vaccine dose, about 10 μg to about 250 μg per vaccine dose, about 10 μg to about 100 μg per vaccine dose, about 20 μg to about 100 μg per vaccine dose, or about 30 μg to about 100 μg per vaccine dose. in some aspects, the amount of immune modulatory molecules is about 500 μg per vaccine dose. In some aspects, the amount of immune modulatory molecules is about 250 μg per vaccine dose.

In aspects of the invention, the amount of the immune modulatory molecule relative to the amount of cholesterol is greater than the amount of cholesterol. In aspects of the invention, the ratio of the amount of the immune modulatory molecule to the amount of cholesterol is about 100:1, or about 75:1, or about 50:1, or about 25:1, or about 15:1, or about 10:1, or about 5:1 by weight. In aspects of the invention, the amount of the immune modulatory molecule relative to the amount of cholesterol is about the same as the amount of cholesterol. That is, the amount of the immune modulatory molecule to the amount of cholesterol is in a ratio of about 1:1 by weight. In aspects of the invention, the amount of the immune modulatory molecule relative to the amount of cholesterol is less than the amount of cholesterol. In aspects of the invention, the ratio of the amount of the immune modulatory molecule to the amount of cholesterol is about 1:100, or about 1:75, or about 1:50, or about 1:25, or about 1:15, or about 1:10, or about 1:5 by weight. In one aspect, the ratio of the amount of the immune modulatory molecule to the amount of cholesterol is about 1:10 by weight. One skilled in the art would realize that the ratios given can be as shown or can be approximately as shown.

As used herein, the terms "disorder", "condition" and "disease" are used interchangeably.

In aspects of the invention, the vaccines are useful as a prophylactic vaccine for the prevention of an infection (e.g., an infectious disease), a disorder associated with a self antigen, or a disorder associated with an addictive substance. Preferably, prophylactic vaccination is used in subjects that are not diagnosed with the condition for which the vaccine is sought, and more preferably the subjects are considered at risk of developing one of these conditions. For example, the subject may be one that is at risk of developing an infection with an infectious organism, or susceptible to a disorder associated with a self-antigen, or susceptible to a disorder associated with an addictive substance.

A subject at risk, as used herein, is a subject who has any risk of exposure to an infection causing pathogen, a subject having or at risk of developing a chronic or treatment-resistant infectious disease, a subject having or at risk of developing cancer, a subject having or at risk of developing an allergy, a subject having or at risk of developing asthma, a subject having or at risk of developing a disorder associated with an addictive substance, a subject having or at risk of developing a disorder involving abnormal protein folding, or a subject having or at risk of developing an autoimmune disorder. A subject at risk also includes subjects that have a predisposition to developing such disorders. Some predispositions can be genetic (and can thereby be identified either by genetic analysis or by family history). Some predispositions are environmental (e.g., prior exposure to infectious agents, self antigens or addictive substances). For a subject at risk of developing an infection, an example of such a subject is a subject living in or expecting to travel to an area where a particular type of infectious agent is or has been found, or it may be a subject who through lifestyle or medical procedures is exposed to an organism either directly or indirectly by contact with bodily fluids that may contain infectious organisms. Subjects at risk of developing infection also include general populations to which a medical agency recommends vaccination for a particular infectious organism.

A subject is a human or a non-human animal treated by veterinarian medicine. Non-human animal subjects include, but are not limited to, a dog, a cat, a bird, a horse, a cow, a pig, a sheep, a goat, a chicken, a non-human primate (e.g., monkey, chimpanzee) and a fish (aquaculture species, e.g., salmon).

An infectious disease, as used herein, is a disease arising from the presence of a foreign microorganism in the body, for example, a bacteria, a virus, a parasite or a fungus.

In aspects of the invention, a bacteria includes, but is not limited to, Aceinetobacter calcoaceticus, Acetobacter paseruianus, Actinobacillus actinomycetemcomitans, Actinobacillus pleuropneumoniae, Actinomyces israelii, Actinomyces viscosus, Aeromonas hydrophila, Alcaliges eutrophus, Alicyclobacillus acidocaldarius, Arhaeglobus fulgidus, Bacillus species, Bacillus antracis, Bacillus pumilus, Bacillus stearothermophillus, Bacillus subtilis, Bacillus thermocatenulatus, Bacteroides species, Bordetella species, Bordetella bronchiseptica, Borrelia burgdorferi, Brucella species, Burkholderia cepacia, Burkholderia glumae, Brachyspira species. Brachyspira hyodysenteria, Brachyspira pilosicoll, Camphylobacter species, Campylobacter coli, Campylobacter fetus, Campylobacter hyointestinalis, Campylobacter jejuni, Chlamydia psittaci, Chlamydia trachomatis, Chlamydophila species, Chromobacterium viscosum, Clostridium species, Clostridium botulinum, Clostridium difficile, Clostridium perfringens, Clostridium tetani, Corynebacterium species, Corynebacterium diphtheriae, Ehrlichia canis, Enterobacter species, Enterobacter aerogenes, Enterococcus species, Erysipelothrix rhusiopathieae, Escherichia species, Escherichia coli, Fusobacterium nucleatum, Haemophilus species, Haemophilus influenzae, Haemophilus somnus, Helicobacter species, Helicobacter pylori, Helicobacter suis, Klebsiella species, Klebsiella pneumoniae, Lactobacillus acidophilis, Lawsonia intracellularis, Legionella species, Legionella pneumophilia, Leptospira species, such as Leptospira canicola, Leptospira grippotyposa, Leptospira hardjo, Leptospira borgpetersenii hardjo-bovis, Leptospira borgpetersenii hardjo-prajitno, Leptospira interrogans, Leptospira icterohaemorrhagiae, Leptospira pomona, Leptospira, Leptospira bratislava, Listeria species, Listeria monocytogenes, Meningococcal bacteria, Moraxella species, Mycobacterium species, Mycobacterium bovis, Mycobacterium tuberculosis, Mycobacterium avium, Mycobacterium intracellulare, Mycobacterium kansaii, Mycobacterium gordonae, Mycoplasma species, such as, Mycoplasma hyopneumoniae, Mycoplasma synoviae, Mycoplasma hyorhinis, Mycoplasma pneumoniae, Mycoplasma mycoides subsp. mycoides LC, Neisseria species, Neisseria gonorrhoeae, Neisseria meningitidis, Odoribacter denticanis, Pasteurella species, Pasteurella (Mannheimia) haemolytica, Pasteurella multocida, Photorhabdus luminescens, Porphyromonas gingivalis, Porphyromonas gulae, Porphyromonas salivosa, Propionibacterium acnes, Proteus species, Proteus vulgaris, Pseudomonas species, Pseudomnas wisconsinensis, Pseudomonas aeruginosa, Pseudomonas fluorescens C9, Pseudomonas fluorescens SIKW1, Pseudomonas Tragi, Pseudomonas luteola, Pseudomonas oleovorans, Pseudomonas sp B11-1, Psychrobacter immobilis, Rickettsia spp, Rickettsia prowazekii, Rickettsia rickettsia, Salmonella species, Salmonella bongori, Salmonella choleraeuis, Salmonella dublin, Salmonella enterica, Salmonella newport, Salmonella typhimurium, Salmonella typhi, Serratia marcescens, Shigella species, Spirlina platensis, Staphylococci species, Staphlyoccocus aureus, Staphyloccoccus epidermidis, Staphylococcus hyicus, Streptococcus species, Streptobacillus moniliformis, beta-hemolytic Streptococcus, Streptococcus pyogenes (Group A Streptococcus), Streptococcus agalactiae (Group B Streptococcus), Streptococcus (viridans group), Streptococcus faecalis, Streptococcus bovis, Streptococcus uberis, Streptococcus dysgalactiae, Streptococcus (anaerobic sps.), Streptococcus pneumoniae, Streptococcus mutans, Streptococcus sobrinus, Streptococcus sanguis, Streptomyces albus, Streptomyces cinnamoneus, Streptomyces exfoliates, Streptomyces scabies, Sulfolobus acidocaldarius, Syechocystis sp., Treponena species, Treponema denticola, Treponema minutum, Treponema palladium, Treponema pertenue, Treponema phagedenis, Treponema refringens, Treponema vincentii, Vibrio species, Vibrio cholerae, Yersinia species and combinations thereof.

In aspects of the invention, a virus includes, but is not limited to, Avian herpesvirus, Avian influenza, Avian leukosis virus, Avian paramyxoviruses, Border disease virus, Bovine coronavirus, Bovine ephemeral fever virus, Bovine herpes viruses, Bovine immunodeficiency virus, Bovine leukemia virus, Bovine parainfluenza virus 3, Bovine respiratory syncytial virus, Bovine viral diarrhea virus (BVDV), BVDV Type I, BVDV Type II, Canine adenovirus, Canine coronavirus (CCV), Canine distemper virus, Canine herpes viruses, Equine herpes viruses, Canine influenza virus, Canine parainfluenza virus, Canine parvovirus, Canine respiratory coronavirus, Classical swine fever virus, Eastern Equine encephalitis virus (EEE), Equine infectious anemia virus, Equine influenza virus, West nile virus, Feline Calicivirus, Feline enteric coronavirus, Feline immunodeficiency virus, Feline infectious peritonitis virus, Feline herpes Virus, Feline influenza virus, Feline leukemia virus (FeLV), Feline viral rhinotracheitis virus, Lentivirus, Marek's disease virus, Newcastle Disease virus, Ovine herpesviruses, Ovine parainfluenza 3, Ovine progressive pneumonia virus, Ovine pulmonary adenocarcinoma virus, Pantropic CCV, Porcine circovirus (PCV) Type I, PCV Type II, Porcine epidemic diarrhea virus, Porcine hemagglutinating encephalomyletitis virus, Porcine herpesviruses, Porcine parvovirus, Porcine reproductive and respiratory syndrome (PRRS) Virus, Pseudorabies virus, Rabies, Rotovirus, Rhinoviruses, Rinderpest virus, Swine influenza virus, Transmissible gastroenteritis virus, Turkey coronavirus, Venezuelan equine encephalitis virus, Vesicular stomatitis virus, West Nile virus, Western equine encephalitis virus and combinations thereof.

In aspects of the invention, a parasite includes, but is not limited to, a protein from Anaplasma, Fasciola hepatica (liver fluke), Coccidia, Eimeria spp., Neospora caninum, Toxoplasma gondii, Giardia, Dirofilaria (heartworms), Ancylostoma (hookworms), Trypanosoma spp., Leishmania spp., Trichomonas spp., Cryptosporidium parvum, Babesia, Schistosoma, Taenia, Strongyloides, Ascaris, Trichinella, Sarcocystis, Hammondia, or Isopsora, and combinations thereof. In aspects, a parasite includes, but is not limited to, ticks, including Ixodes, Rhipicephalus, Dermacentor, Amblyomma, Boophilus, Hyalomma, or Haemaphysalis species, and combinations thereof.

In aspects of the invention, a fungus includes, but is not limited to, spores, molds and yeasts (for example, Candida species).

A chronic or treatment-resistant infectious disease, as used herein, is a disease having a prolonged infection period, sometimes lasting weeks, months and even a lifetime, or an infection that resists other treatments that are usually successful. In some aspects, a chronic or treatment-resistant viral infection includes, but is not limited to, HBV, HCV, HIV, HPV, HSV-1 or HSV-2.

In aspects of the invention, a subject having a cancer is a subject that has detectable cancerous cells. The cancer may be a malignant or non-malignant cancer. Cancers or tumors include, but are not limited to, biliary tract cancer; bladder cancer; brain cancer; breast cancer; cervical cancer; choriocarcinoma; colon cancer; colorectal cancer; endometrial cancer; esophageal cancer; gastric cancer; glioblastoma; intraepithelial neoplasms; lymphomas (for example, follicular lymphoma); liver cancer; lung cancer (for example, small cell and non-small cell); leukemia (for example, hairy cell leukemia, chronic myelogenous leukemia, cutaneous T-cell leukemia); melanoma (for example, malignant melanoma); multiple myeloma; neuroblastomas; oral cancer; ovarian cancer; pancreas cancer; prostate cancer; rectal cancer; renal cancer; sarcomas; skin cancer; testicular cancer; thyroid cancer; and renal cancer, as well as other carcinomas and sarcomas (for example, squamous cell carcinoma, renal cell carcinoma, prostate carcinoma, bladder cell carcinoma, or colon carcinoma).

In aspects of the invention, a subject having an allergy is a subject that has or is at risk of developing an allergic reaction in response to an allergen. An allergy refers to acquired hypersensitivity to a substance (allergen). Allergic conditions include, but are not limited to, eczema, allergic rhinitis or coryza, hay fever, conjunctivitis, bronchial asthma, urticaria (hives) and food allergies, and other atopic conditions.

Currently, allergic diseases are generally treated by the injection of small doses of antigen followed by subsequent increasing dosage of antigen. It is believed that this procedure induces tolerization to the allergen to prevent further allergic reactions. These methods, however, can take several years to be effective and are associated with the risk of side effects such as anaphylactic shock.

Allergies are generally caused by IgE antibody generation against harmless allergens. The cytokines that are induced by systemic or mucosal administration of immunostimulatory nucleic acids are predominantly of a class called Th1 (examples are IL-12 and IFN-.gamma.) and these induce both humoral and cellular immune responses. The types of antibodies associated with a Th1 response are generally more protective because they have high neutralization and opsonization capabilities. The other major type of immune response, which is associated with the production of IL-4, IL-5 and IL-10 cytokines, is a Th2 immune response. Th2 responses involve predominately antibodies and these have less protective effect against infection and some Th2 isotypes (e.g., IgE) are associated with allergy. In general, it appears that allergic diseases are mediated by Th2 type immune responses while Th1 responses provide the best protection against infection, although excessive Th1 responses are associated with autoimmune disease. Based on the ability of the one or more immune modulatory molecules to shift the immune response in a subject from a Th2 (which is associated with production of IgE antibodies and allergy) to a Th1 response (which is protective against allergic reactions), an effective dose for inducing an immune response of a immune modulatory molecule can be administered to a subject to treat or prevent an allergy.

In aspects of the invention, an allergen refers to a substance (for example, an antigen) that can induce an allergic or asthmatic response in a susceptible subject. Allergens include, but are not limited to, pollens, insect venoms, animal dander dust, fungal spores and drugs (e.g. penicillin). Examples of natural, animal and plant allergens include, but are not limited to, proteins specific to the following genuses: *Canine* (*Canis familiaris*); *Dermatophagoides* (e.g. *Dermatophagoides farinae*); *Felis* (*Felis domesticus*); *Ambrosia* (*Ambrosia artemiisfolia; Lolium* (e.g. *Lolium perenne* or *Lolium multiflorum*); *Cryptomeria* (*Cryptomeria japonica*); *Alternaria* (*Alternaria alternata*); *Alder; Alnus* (*Alnus gultinoasa*); *Betula* (*Betula verrucose*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalls* or *Parietaria judaica*); *Blattella* (e.g. *Blattella germanica*); *Apis* (e.g. *Apis multiflorum*); *Cupressus* (e.g. *Cupressus sempervirens, Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elafior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*).

In aspects of the invention, asthma refers to a disorder of the respiratory system characterized by inflammation, narrowing of the airways and increased reactivity of the airways to inhaled agents. Th2 cytokines, for example, IL-4 and IL-5 are elevated in the airways of asthmatic subjects. These cytokines promote important aspects of the asthmatic inflammatory response, including IgE isotype switching, eosinophil chemotaxis and activation and mast cell growth. Th1 cytokines, especially IFN-.gamma. and IL-12, can suppress the formation of Th2 clones and production of Th2 cytokines. Asthma is frequently, although not exclusively, associated with atopic or allergic symptoms.

In aspects of the invention, a disorder involving abnormal protein folding is a disorder resulting from an associated protein either misfolding or an error in a subject's DNA leading to the incorrect folding of a protein. In aspects, a disorder involving abnormal protein folding is an amyloidose disorder, for example, Alzheimer's disease, MS, or a prion disorder, for example transmissable spongiform encephalopathies (TSEs), which include, but are not limited to, bovine spongiform encephalopathy (BSE, mad cow disease) and Creutzfeld Jakob disease (CJD) in humans. In aspects, a disorder involving an error in a subject's DNA leading to the incorrect folding of a protein includes, but is not limited to, cystic fibrosis and cancers associated with the p53 protein.

In aspects of the invention, an autoimmune disorder is any disorder involving an overactive immune response of the subject's body against substances and tissues (for example, a self antigen) normally present in the subject. In some aspects, an autoimmune disorder is Rheumatoid arthritis (RA), lupus or Crohn's disease.

In aspects of the invention, a disorder associated with a self antigen is any disorder that is caused by an antigen of a subject's own cells or cell products that causes an immune response in said subject. For example, in some embodiments, a self antigen is a tumor antigen, an antigen associated with Alzheimer's Disease, an antigen against an antibody, or an antigen that is expressed from human endogenous retroviral elements. In some aspects, the tumor antigen is one or more of WT1, MUC1, LMP2, HPV E6 or HPV E7, EGFR or variant form thereof, for example, EGFRvIII, HER-2/neu, Idiotype, MAGE A3, p53 non-mutant, NY-ESO-1, PSMA, GD2, CEA, MelanA/MART1, Ras mutant, gp100, p53 mutant, Proteinase3 (PR1), bcr-abl, Tyrosinase, Survivin, PSA, hTERT, Sarcoma translocation breakpoints, EphA2, PAP, ML-IAP, AFP, EpCAM, ERG (TMPRSS2 ETS fusion gene), NA17, PAX3, ALK, Androgen receptor, Cyclin B1, polysialic acid, MYCN, RhoC, TRP-2, GD3, Fucosyl GM1, Mesothelin, PSCA, MAGE Al, sLe (animal), CYP1B1, PLAC1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, B7H3, Legumain, Tie 2, Page4, VEGFR2, MAD-CT-1, FAP, PDGFR-beta, MAD-CT-2, or Fos-related antigen 1. An antigen associated with Alzheimer's Disease may be tau or β-amyloid. An antigen against an antibody may be an antigen against a human antibody, for example, in some embodiments the antigen is IgE.

In aspects of the invention, the vaccines may be used in the prevention of a respiratory viral infection in an animal. In some aspects, the respiratory viral infection is BVDV 1, BVDV 2, IBRV, PI3V or BRSV.

In aspects of the invention, a disorder associated with an addictive substance is any disorder that involves a subject developing an addiction to an addictive chemical or biological substance. For example, in some embodiments, an addictive substance may be nicotine or cocaine. In some embodiments, the vaccine to prevent or treat the addiction contains nicotine or a nicotine-like hapten conjugated to a carrier. In some embodiments, the carrier to which a nicotine or nicotine-like hapten is conjugated is a bacterial toxoid or derivative, *Pseudomonas* exotoxin, KLH or a virus-like particle. In some aspects, the bacterial toxoid is diphtheria toxoid or a derivative thereof, for example, $CRM_{197}$. In some aspects, the virus-like particle is HBsAg, HBcAg, *E. coli* bacteriophage Qβ, Norwalk virus or influenza HA.

As used herein, the term "treat", "treated" or "treating" when used with respect to an infectious disease refers to a prophylactic treatment which increases the resistance of a subject (a subject at risk of infection) to infection with a pathogen, or in other words, decreases the likelihood that the subject will become infected with the pathogen as well as a treatment after the subject (a subject who has been infected) has become infected in order to fight the infection, e.g., reduce or eliminate the infection or prevent it from becoming worse.

The term "treat", "treated" or "treating" when used with respect to a cancer refers to a prophylactic treatment which increases the resistance of a subject (a subject at risk of developing cancer) to cancer, or decreases the likelihood that the subject will develop cancer as well as a treatment after the subject (a subject who has or is diagnosed with cancer) has developed such a disorder or begun to develop signs or symptoms of developing such a disorder, to reduce the effect of the disorder, e.g., reduce or eliminate the signs or symptoms associated with the disorder or prevent them from becoming worse.

The term "treat", "treated" or "treating" when used with respect to asthma or allergy refers to a prophylactic treatment which increases the resistance of a subject (a subject at risk of developing asthma or allergy) to develop such a disorder or decreases the likelihood that the subject will develop asthma or allergy as well as a treatment after the subject (a subject who has or is diagnosed with asthma or allergy) has developed such a disorder or begun to develop signs or symptoms of developing such a disorder, to reduce the effect of the disorder, e.g., reduce or eliminate the signs or symptoms associated with the disorder or prevent them from becoming worse.

The term "treat", "treated" or "treating" when used with respect to a disorder associated with an addictive substance refers to a prophylactic treatment which increases the resistance of a subject (a subject at risk of a disorder associated with an addictive substance) to develop such a disorder or decreases the likelihood that the subject will develop the disorder associated with an addictive substance as well as treatment after the subject (a subject who has or is diagnosed with a disorder associated with an addictive substance) has developed such a disorder or begun to develop signs or symptoms of developing such a disorder, to reduce the effect of the disorder, e.g., reduce or eliminate the signs or symptoms associated with the disorder or prevent them from becoming worse.

The term "treat", "treated" or "treating" when used with respect to a disorder associated with abnormal protein folding refers to a prophylactic treatment which increases the resistance of a subject (a subject at risk of a disorder associated with abnormal protein folding) to develop such a disorder or decreases the likelihood that the subject will develop the disorder associated with abnormal protein folding as well as treatment after the subject (a subject who has or is diagnosed with a disorder associated with abnormal protein folding) has developed such a disorder or begun to develop signs or symptoms of developing such a disorder, to reduce the effect of the disorder, e.g., reduce or eliminate the signs or symptoms associated with the disorder or prevent them from becoming worse.

The term "treat", "treated" or "treating" when used with respect to an autoimmune disorder refers to a prophylactic treatment which increases the resistance of a subject (a subject at risk of an autoimmune disorder) to develop such a disorder or decreases the likelihood that the subject will develop the autoimmune disorder as well as treatment after the subject (a subject at who has or is diagnosed with an autoimmune disorder) has developed such a disorder or begun to develop signs or symptoms of developing such a disorder, to reduce the effect of the disorder, e.g., reduce or eliminate the signs or symptoms associated with the disorder or prevent them from becoming worse.

The term "treat", "treated" or "treating" when used with respect to a disorder associated with a self antigen refers to a prophylactic treatment which increases the resistance of a subject (a subject at risk of a disorder associated with a self antigen) to develop such a disorder or decreases the likelihood that the subject will develop the disorder associated with a self antigen as well as treatment after the subject (a subject who has or is diagnosed with a disorder associated with a self antigen) has developed such a disorder or begun to develop signs or symptoms of developing such a disorder, to reduce the effect of the disorder, e.g., reduce or eliminate the signs or symptoms associated with the disorder or prevent them from becoming worse.

The treatment of a subject or with the vaccines as described herein, results in the reduction of infection or the complete abolition of the infection, reduction of the signs/symptoms associated with a disorder associated with a self antigen or the complete abolition on the disorder, or reduction of the signs/symptoms associated with a disorder associated with an addictive substance or the complete abolition of the disorder. A subject may be considered as treated if such symptoms related to the infectious disease, cancer, allergy, asthma, disorder associated with abnormal protein folding, autoimmune disorder, disorder associated with a self antigen or disorder associated with an addictive substance, are reduced, are managed or are abolished as a result of such treatment. For an infectious disease, such treatment also encompasses a reduction in the amount of infectious agent present in the subject (e.g., such amounts can be measured using standard assays such as ELISA known to those of ordinary skill in the art). For a cancer, such treatment also encompasses a reduction in the cancerous cells or tissues, and/or a reduction in the signs/symptoms associated with the cancer. For an allergy, such treatment also encompasses a reduction in the signs/symptoms associated with the allergy. For an asthma, such treatment also encompasses a reduction in the signs/symptoms associated with the asthma. For an autoimmune disorder, such treatment also encompasses a reduction in the immune response against the autoimmune disorder, and/or a reduction in the signs/symptoms associated with the disorder. For a disorder associated with abnormal protein folding, such treatment also encompasses a reduction in the amount of abnormal protein, and/or a reduction or reversal in the signs/symptoms associated with the disorder. For a disorder associated with a self antigen, such treatment also encompasses a reduction in the amount of self antigen present in the subject or a reduction in the immune response induced as a result of the self antigen. For a disorder associated with an addictive substance, such treatment also encompasses a reduction in the signs/symptoms associated with addiction to an addictive substance.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients. For certain vaccine formulations using cholesterol, ethanol may be substituted with a pharmaceutically acceptable surfactant and water solution to solubilize the cholesterol into an aqueous formulation.

For use in therapy, an effective amount of the one or more immune modulatory molecules can be administered to a subject by any mode that delivers the immune modulatory molecule to the desired surface. Administering the pharmaceutical composition of the present invention may be accomplished by any means known to the skilled artisan. Preferred routes of administration include but are not limited to parenteral (for example, intramuscular, subcutaneous, intradermal, intravenous injection), topical to the skin (for example, transdermal) or mucosal (for example, oral, intranasal, intravaginal, intrarectal, trans-buccal, intraocular or sublingual). In the case of treatment of cancers, this may include intra-tumor administrations.

In aspects of the invention, "effective amount" of an immune modulatory molecule refers to the amount necessary or sufficient to realize a desired biologic effect. For example, an effective amount of an immune modulatory molecule for treating a disorder could be that amount necessary to eliminate a microbial infection or a tumor. An effective amount for use as a vaccine adjuvant could be that amount useful for boosting a subject's immune response to a vaccine. An "effective amount" for treating an infectious disease, a cancer, an allergy, asthma, an autoimmune disorder, a disorder associated with abnormal protein folding, a disorder associated with a self antigen or a disorder associated with an addictive substance can be that amount useful for inducing an antigen-specific immune response. The effective amount for any particular application can vary depending on such factors as the disease or condition being treated, the particular an immune modulatory molecule being administered, the size of the subject, or the severity of the disease or condition. One of ordinary skill in the art can empirically determine the effective amount of a particular an immune modulatory molecule without necessitating undue experimentation.

Subject doses of the compounds described herein for local delivery typically range from about 0.1 µg to about 50 mg per administration which, depending on the application, could be given daily, weekly, or monthly and any other amount of time therebetween. More typically local doses range from about 10 µg to about 10 mg per administration, and optionally from about 100 µg to about 1 mg, with 2-4 administrations being spaced days or weeks apart. More typically, immune stimulant doses range from about 1 µg to about 10 mg per administration, and most typically about 10 µg to about 1 mg, with daily or weekly administrations. Subject doses of the compounds described herein for parenteral delivery for the purpose of inducing an antigen-specific immune response, wherein the compounds are delivered with an antigen but not another therapeutic agent are typically about 5 to about 10,000 times higher than the effective local dose for vaccine adjuvant or immune stimulant applications, and more typically about 10 to about 1,000 times higher, and most typically about 20 to about 100 times higher. Doses of the compounds described herein for parenteral delivery, e.g., for inducing an innate immune response, for increasing ADCC, for inducing an antigen specific immune response when the one or more immune modulatory molecules are administered in combination with other therapeutic agents or in specialized delivery vehicles typically range from about 0.1 µg to about 10 mg per administration which, depending on the application, could be given daily, weekly, or monthly and any other amount of time therebetween. More typically parenteral doses for these purposes range from about 10 µg to about 5 mg per administration, and most typically from about 100 µg to about 1 mg, with 2-4 administrations being spaced days or weeks apart. In some embodiments, however, parenteral doses for these purposes may be used in a range of about 5 to about 10,000 times higher than the typical doses described above.

For any compound described herein the therapeutically effective amount can be initially determined from animal models. A therapeutically effective dose can also be determined from human data for immune modulatory molecules which have been tested in humans (e.g., human clinical trials have been initiated) and for compounds which are known to exhibit similar pharmacological activities, such as other adjuvants, e.g., LT and other antigens for vaccination purposes. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The one or more immune modulatory molecules either alone or with one or more antigens, cholesterol or other therapeutic agents, may be administered via any route described herein.

The one or more immune modulatory molecules, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the immune modulatory molecules in water-soluble form. Additionally, suspensions of the immune modulatory molecules may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the immune modulatory molecules to allow for the preparation of highly concentrated solutions.

One may dilute or increase the volume of the therapeutic with an inert material. These diluents could include carbohydrates, especially mannitol, a-lactose, anhydrous lactose, cellulose, sucrose, modified dextrans and/or starch. Certain inorganic salts may be also be used as fillers including calcium triphosphate, magnesium carbonate and/or sodium chloride. Some commercially available diluents are Fast-Flo, Emdex, STA-Rx 1500, Emcompress and Avicell.

To aid dissolution of the therapeutic into the aqueous environment a surfactant might be added as a wetting agent. Surfactants may include anionic detergents such as sodium lauryl sulfate, dioctyl sodium sulfosuccinate and/or dioctyl sodium sultanate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and/or 60, glycerol monostearate, polysorbate 40, 60, 65 and/or 80, sucrose fatty acid ester, methyl cellulose and carboxymethyl cellulose. In aspects, non-ionic detergents include, but are not limited to, octoxynols, for example, t-octylphenoxy polyethoxyethanol (TRITON X-100™), polyoxyethylene esters, for example, polyoxyethylene sorbitan monooleate (TWEEN 80™, bile salts and cholic acid derivatives, for example sodium deoxycholate or taurodeoxycholate. In aspects, a formulation may comprise 3D-MPL, laureth 9, TRITON X 100™, TWEEN 80™, and sodium deoxycholate. These surfactants could be present in the formulation of the immune modulatory molecules either alone or as a mixture in different ratios.

Pharmaceutical formulations for parenteral administration include aqueous solutions of the immune modulatory molecules in water-soluble form. Additionally, suspensions of the immune modulatory molecules may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the immune modulatory molecules to allow for the preparation of highly concentrated solutions.

Alternatively, the immune modulatory molecules may be in powder form for constitution with a suitable vehicle, e.g., sterile pyrogen-free water, before use.

For oral administration, the compounds (for example, immune modulatory molecules alone or with one or more antigens, cholesterol and/or other therapeutic agents) can be formulated readily by combining the immune modulatory molecules with pharmaceutically acceptable carriers well known in the art. Such carriers enable the immune modulatory molecules of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also contemplated are oral dosage forms of the above agents or formulations. The agents or formulations may be chemically modified so that oral delivery of the derivative is efficacious. Generally, the chemical modification contemplated is the attachment of at least one moiety to the agent or formulation itself, where said moiety permits (a) inhibition of proteolysis; and (b) uptake into the blood stream from the stomach or intestine. Also desired is the increase in overall stability of the agent or formulation and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl, Biochem. 4:185-189. Other polymers that could be used are poly-1,3-dioxolane and poly-1,3,6-tioxocane. Preferred for pharmaceutical usage, as indicated above, are polyethylene glycol moieties.

Intranasal delivery of a pharmaceutical composition of the present invention is also contemplated. Intranasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran. In aspects, a formulation for intranasal delivery (or mucosal delivery) may comprise 3D-MPL, laureth 9, TRITON X-100™, TWEEN 80™, and sodium deoxycholate. In aspects, such a formulation may be combined with an antigen, for example an influenza virus antigen.

For intranasal administration, a useful device is a small, hard bottle to which a metered dose sprayer is attached. In aspects, the metered dose is delivered by drawing the pharmaceutical composition of the present invention solution into a chamber of defined volume, which chamber has an aperture dimensioned to aerosolize an aerosol formulation by forming a spray when a liquid in the chamber is compressed. The chamber is compressed to administer the pharmaceutical composition of the present invention. In aspects, the chamber is a piston arrangement. Such devices are commercially available.

Alternatively, a plastic squeeze bottle with an aperture or opening dimensioned to aerosolize an aerosol formulation by forming a spray when the bottle is squeezed. The opening is usually found in the top of the bottle, and the top is generally tapered to partially fit in the nasal passages for efficient administration of the aerosol formulation. In aspects, the nasal inhaler will provide a metered amount of the aerosol formulation, for administration of a measured dose of the drug.

For trans-buccal administration, the compositions may take the form of tablets or lozenges formulated in conventional manner.

The compounds may also be formulated in rectal or vaginal compositions such as suppositories or retention enemas, e.g., containing conventional suppository bases such as cocoa butter or other glycerides.

In addition to the formulations described, the compounds may also be formulated as a depot preparation. Such long acting formulations may be formulated with suitable polymeric or hydrophobic materials (for example, as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249:1527-1533, 1990.

The immune modulatory molecules and optionally other therapeutics and/or antigens may be administered per se (neat) or in the form of a pharmaceutically acceptable salt. When used in medicine, the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

In aspects of the invention, the formulations may also comprise a bile acid or a derivative thereof. In aspects, this may be in the form of a salt. In aspects, derivatives include, but are not limited to, derivatives of cholic acid and salts thereof. In aspects, sodium salts of cholic acid or cholic acid derivatives are contemplated. In aspects, bile acids and derivatives thereof include, but are not limited to, cholic acid, deoxycholic acid, chenodeoxycholic acid, lithocholic acid, ursodeoxycholic acid, hyodeoxycholic acid and derivatives for example, glyco-, tauro-, amidopropyl-1-propanesulfonic-, amidopropyl-2-hydroxy-1-propanesulfonic derivatives of the aforementioned bile acids, or N,N-bis(3D gluconoamidopropyl) deoxycholamide. In aspects, sodium deoxycholate (NaDOC) may be present in a vaccine of the invention.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzaikonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of one or more immune modulatory molecules and optionally one or more antigens, cholesterol and/or other therapeutic agents optionally included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference in their entireties.

EXAMPLES

Example 1

Cholesterol as a Delivery Vehicle for CpG ODN Immunogenicity & Efficacy Data

The use of liposomes containing cationic lipids with cholesterol has shown enhanced efficacy of CpG ODN. The use of cholesterol microspheres, without additional lipids, was tested as an adjuvant for augmenting cellular immunity. C57Bl/6 mice (n=5 per group) were immunized intramuscularly on days 0, 14 and 21 with ovalbumin (10 µg), CpG alone (CPG 24555, 10 µg), and CpG (CpG 24555, 10 µg) with cholesterol (1 µg). Antigen specific T cells (CD4+ and CD8+) secreting single, double or triple cytokines (IL-2, IFN-γ and TNF-α) were measured on day 28 using flow cytometry.

Figure 1C:
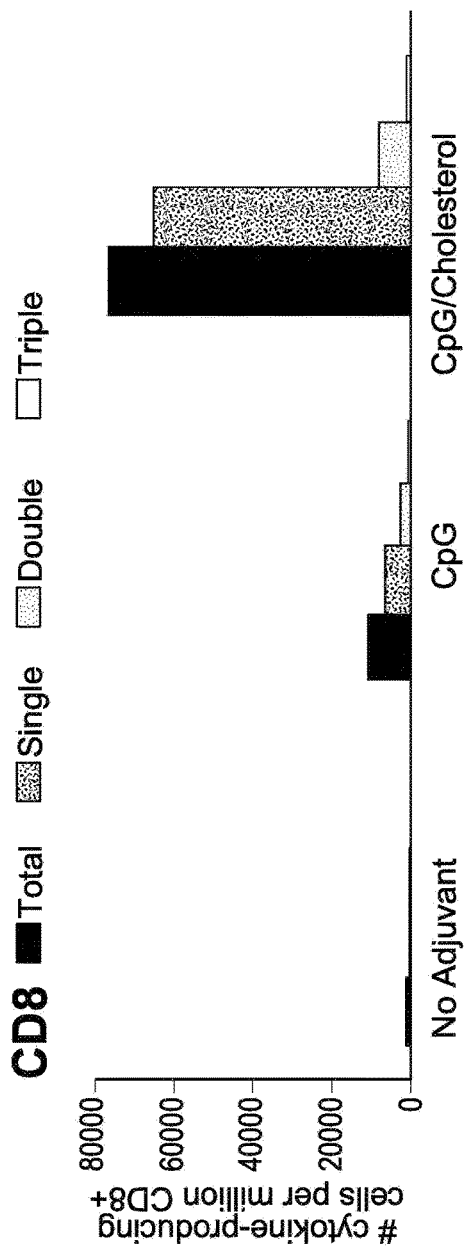
FIG. 1c. Graph of CD8+ T cells secreting single or double cytokines.
Figure 1D:
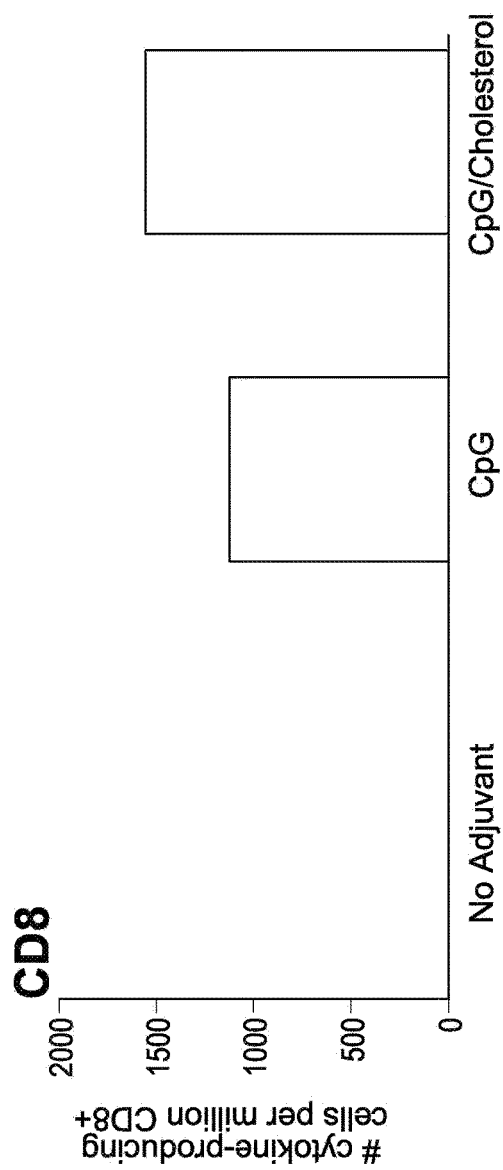
FIG. 1d. Graph of CD8+ T cells secreting triple cytokines.

Results and Discussion:

CpG+cholesterol enhanced the population of poly-functional CD8+ cells compared to CpG alone. CpG alone and CpG+cholesterol resulted in single and double cytokine producing CD4+ cells (FIG. 1a). CpG+cholesterol resulted in triple cytokine producing CD4+ cells (FIG. 1 b). CpG alone and CpG+cholesterol resulted in single, double and triple cytokine producing CD8+ cells (FIGS. 1c and 1d).

Enhanced secretion of antigen specific IL-2 (FIG. 2a) and IFN-γ (FIG. 2b) (Th1-biased cytokines) was shown with CpG+cholesterol. No enhancement in pro-inflammatory or Th2-biased cytokines was shown.

Figure 3A:
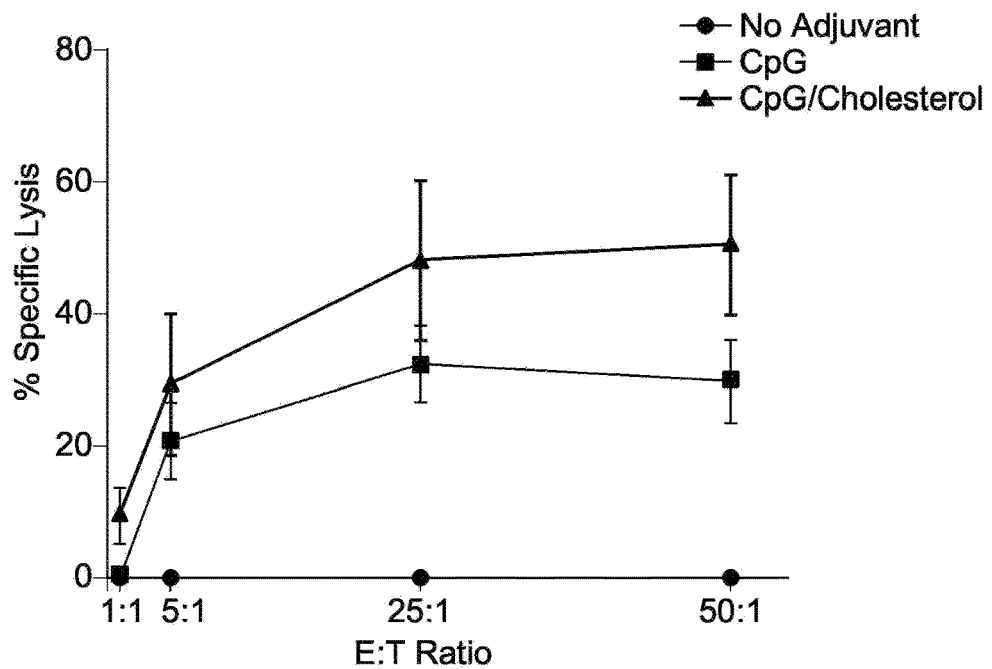
FIGS. 3a-3b: cytotoxic T cell responses.
Figure 3B:
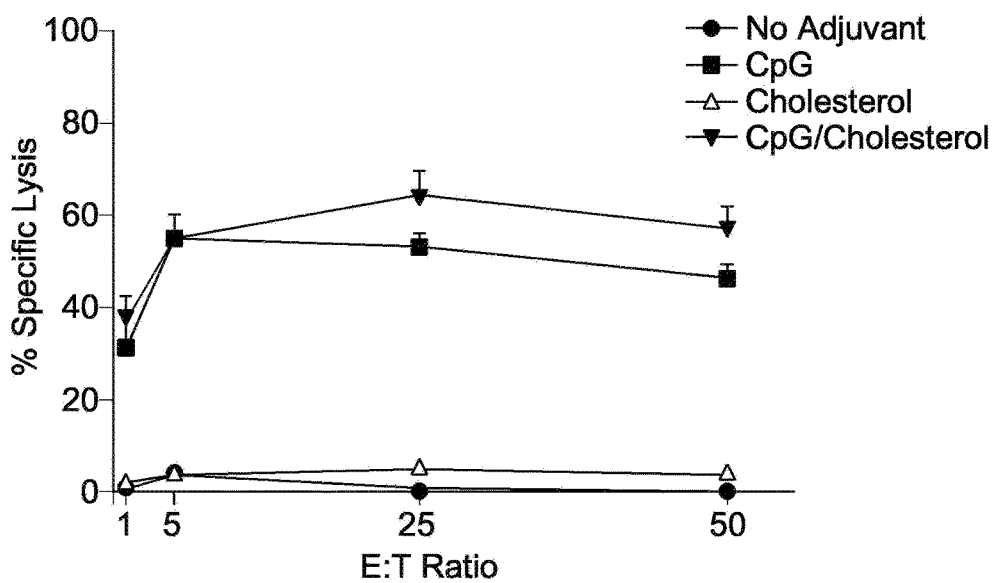
Figure 3C:
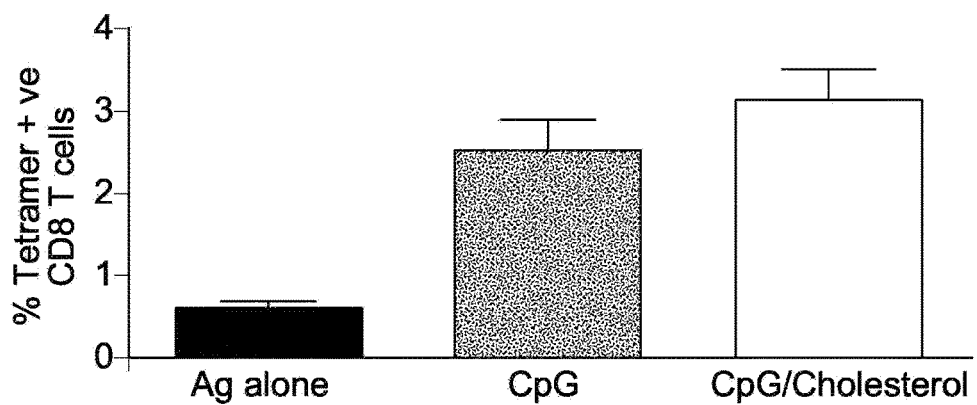
FIGS. 3c-3d: antigen-specific CD8+ T cell population.
Figure 3D:
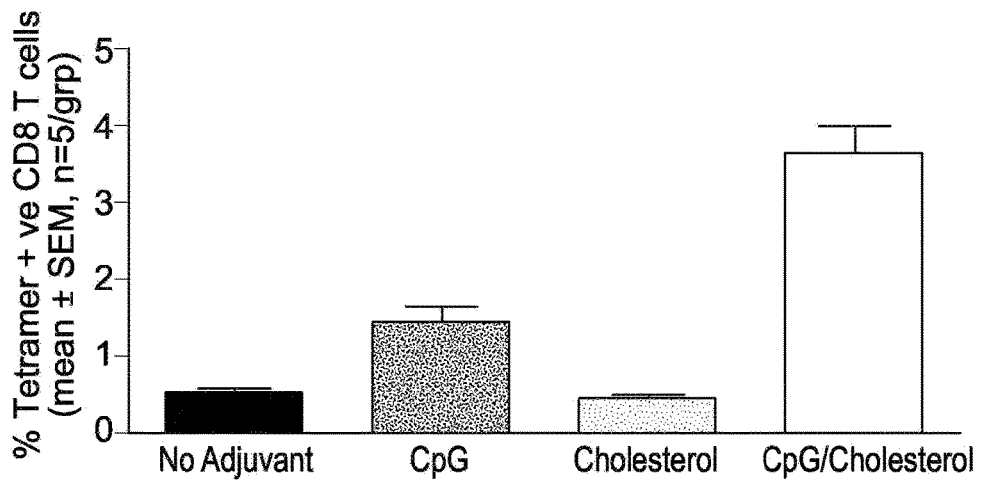

Cytotoxic T lymphocyte responses to CpG alone and CpG+cholesterol were measured. CpG+cholesterol enhanced ovalbumin specific cytotoxic T cell responses (FIGS. 3a and 3b) and antigen-specific CD8 T cell population was increased (FIGS. 3c and 3d) compared to CpG alone. Cholesterol alone showed similar levels to the no adjuvant control.

Figure 4:
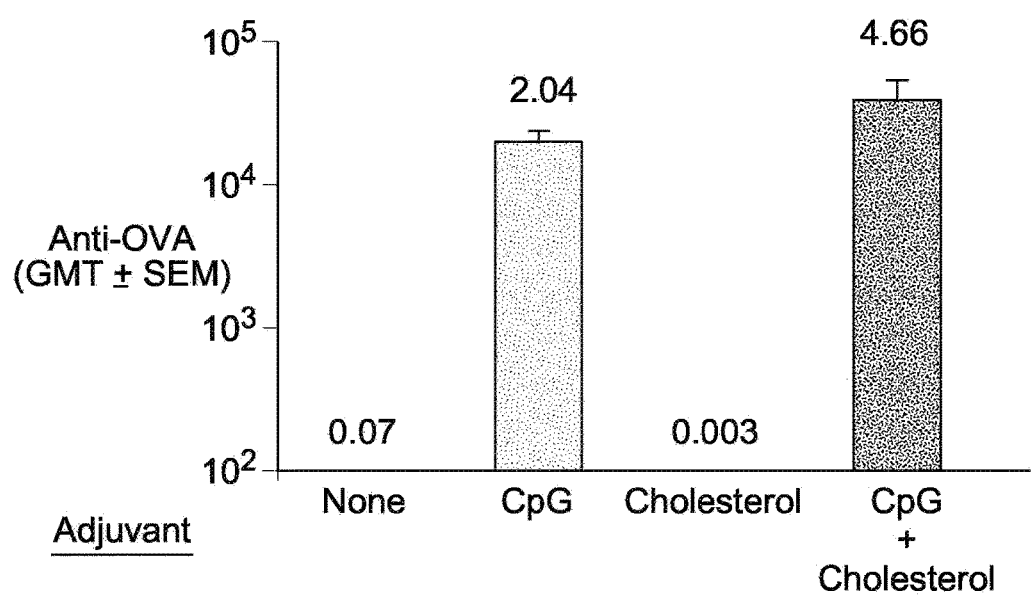
FIG. 4: Graph of ovalbumin specific antibody titers in the presence of no adjuvant or in the presence of CpG or CpG+cholesterol as an adjuvant. The numbers above each bar represent the ratio of IgG2c/IgG1.

Humoral responses to CpG alone and CpG+cholesterol were measured. CpG+cholesterol showed enhanced ovalbumin specific antibody titer and Th1-bias over CpG alone (FIG. 4). The numbers above each bar represent the ratio of IgG2c/IgG1. In mice, a higher IgG2a or 2c is indicative of a Th1 biased immune response whereas a higher IgG1 titer is indicative of a Th2 biased immune response. For CpG and CpG+cholesterol the amount of IgG2c was higher than IgG1 (2.04 and 4.66 respectively) which is indicative of a Th1 biased immune response.

In each case, cholesterol alone showed no significant adjuvant activity.

Co-delivery of antigen and CpG, and antigen with CpG+cholesterol showed no retardation of mobility of CpG in electrophoresis. The same amount of CpG was observed in supernatants of CpG+cholesterol when quantified by UV compared to free CpG. This suggests that there was no strong association of CpG with cholesterol.

Subcutaneous immunization was less effective than intramuscular injection suggesting no evidence for co-delivery. However, co-delivery appears to play some role with a co-formulation of antigen and CpG demonstrating the strongest response.

Figure 5:
FIG. 5: Transmission Electron Microscopy image of antigen, CpG and cholesterol.

Without being limited to a particular theory, transmission electron microscopy (TEM) suggested cholesterol formed insoluble helical micelles that may interact with cell membranes to allow the delivery of CpG (FIG. 5).

Example 2

Immunogenicity, Safety and Efficacy of a Pentavalent (IBR, BRSV, PI3, BVDV 1 & 2) Inactivated Vaccine in Calves Against BVDV-2 Challenge The injection site reactions in calves immunized with a pentavalent inactivated viral vaccine Bovine Virus Diarrhea (BVDV 1&2), Infectious bovine rhinotracheitis (IBRV), Parainfluenza 3 virus (PI3V) and Bovine Respiratory Syncytial virus (BRSV) (respective viral antigen at 15% of 2 ml dose) in the presence of an adjuvant were measured. Adjuvants CpG+cholesterol (at ratios of 1:1 or 1:10 CpG:cholesterol), Advasure-DEAE/Dextran, QCDCR (saponin carrier complex) or QCDCR+CpG were administered. Some animals were immunized with commercial vaccine. Placebo animals received sterile saline. Calves (7/gp; 9-12 months old) were vaccinated at day 0 and day 22 subcutaneously with inactivated 2 ml BVDV 1&2, IBRV, PI3V and BRSV and challenged with 4 ml BVDV-2 (Noncytopathic Bovine Viral Diarrhea Virus Type 2; Strain 24515) intranasally on day 42.

The adjuvants used in the vaccines of each treatment group were as follows: Treatment Group T01 received sterile saline (no adjuvant). Treatment Group T02 received a vaccine in which the adjuvant was the oil-based emulsion contained in a commercial vaccine. Treatment Group T03 received a vaccine in which the adjuvant was CpG-23877 (250 µg)/cholesterol (250 µg), thus providing a ratio of CpG:cholesterol of 1:1. Treatment Group T04 received a vaccine in which the adjuvant was CpG-23877 (250 µg)/cholesterol (2,500 µg), thus providing a ratio of CpG:cholesterol of 1:10. Treatment Group T05 received a vaccine in which the adjuvant was AdvaSure®, an oil-based emulsion containing DEAE-DEXTRAN (100 mg) and ISC (800 µg). Treatment Group T06 received a vaccine in which the adjuvant was Quil A (250 µg), cholesterol (250 µg), dimethyl dioctadecyl ammonium bromide (DDA; 100 µg), Carbopol® (0.0375 µg), and N-(2-Deoxy-2-L-leucylamino-b-D-glucopyranosyl)-N-octadecyldodecanoylamide hydroacetate, also known by the trade name Bay R1005® (1,000 µg). This combination of components is herein referred to as QCDCR. Treatment Group T07 received a vaccine in which the adjuvant was QCDCR (in the amounts given in T06) and CpG 23877 (250 µg).

Blood samples were collected at days 0, 22, 42 and 56 and analysed using ELISA for IgG antibody titers. BVDV ELISA was developed and optimized at PAH using the p67 H fragment of BVDV as antigen. Briefly, NUNC Maxisorp plates were coated with 0.2 ug/ml of recombinant p67 H fragment BVDV antigen in Carbonate-Bicarbonate buffer PH 9.6 and incubated overnight at 4° C. The coating antigen was then discarded and plates damped and blocked using 1% Ovalbumin in PBS-Tween (300 µl/well) for 1 h at 37° C. The blocking buffer was then removed and diluted serum samples added (seven 5-fold serial dilutions; starting at 1:50) and plates incubated for 1 h at 37° C. Plates were washed four times in PBS-T (0.05% Tween 20) before adding 100 µl of sheep anti-bovine IgG-h+l-HRP conjugate in blocking buffer (1:4,000) and incubating for 1 h at room temperature in the dark. Plates were washed again in PBS-T as described above and TMB substrate added (100 µl/well). Following Incubation for 5-10 minutes, the reaction was stopped using 2N Sulfuric acid (50 µl/well) and the Optical Density (OD) measured OD at 450 nM. Results were expressed as Geometric mean titers.

Results and Discussion

The symptoms of BVDV-2 challenge are fever, leukopenia (about a 40% decrease in WBC count from the mean pre-challenge WBC count) from day 3 to 12 after challenge and immune-modulation, thrombocytopenia, respiratory distress, depression, reproduction disorders (abortion) and diarrhea. Protective immunity against BVDV is a Th-1 type immune response. Cell mediated immunity is mediated by CD4+ T cells. CD8+ T cells are important for clearance of the virus and memory responses. IFN-α and IFN-γ are protective against BVDV infection, Vaccines generally should induce CMI and humoral immunity against BVDV. Table 1 depicts the percentage of calves with clinical disease, fever, leukopenia or viremia following challenge with BVDV-2 post vaccination with pentavalent inactivated viral vaccine BVDV 1&2, IBRV, PI3V and BRSV in the presence of CpG+cholesterol (at ratios of 1:1 (T03) or 1:10 (T04) CpG:cholesterol), Advasure-DEAE/Dextran (T05), QCDCR (T06), QCDCR+CpG (T07), commercial vaccine (T02) or sterile saline (T01).

TABLE 1

Percentage of calves with clinical disease, fever, leukopenia or viremia

| Treatment Group | % Clinically Sick | % Fever | % Leukopenic | % Viremic |
| --- | --- | --- | --- | --- |
| Non-vaccinated control (PBS) | 42.9 | 85.7 | 100 | 100 |
| commercial vaccine | 57.1 | 14.3 | 100 | 85.7 |
| 5V + CpG Cholesterol (1:1) | 14.3 | 0 | 42.9 | 28.6 |
| 5V + CpG Cholesterol (1:10) | 0 | 14.3 | 71.4 | 0 |
| 5V + Advasure DEAE-Dextran/ISC | 66.7 | 33.3 | 83.3 | 33.3 |
| 5V + QCDCR | 57.1 | 28.6 | 85.7 | 42.9 |
| 5V + QCDCR-CpG (1:1) | 42.9 | 14.3 | 71.4 | 0 |

Vaccines administered to calves in groups T02 (commercial vaccine), 103 (CpG:cholesterol 1:1), T04 (CpG:cholesterol 1:10), T05 (Advasure-DEAE/Dextran), T06 (QCDCR) and T07 (QCDCR+CpG) were superior at suppressing fever compared with saline controls. Vaccines administered to calves in T03 (CpG:cholesterol 1:1), T04 (CpG:cholesterol 1:10), T05 (Advasure-DEAE/Dextran), T06 (QCDCR) and T07 (QCDCR+CpG) were superior at suppressing viremia compared with commercial vaccine (T02) and saline groups (T01). T04 and T07 suppressed viremia completely and the commercial vaccine (T02) calves were viremic for a shorter period than the controls. Although leukopenia was not totally prevented in any vaccinated group, there was a vaccine effect noted on multiple days between T03 (CpG:cholesterol 1:1), T04 (CpG:cholesterol 1:10), T05 (Advasure-DEAE/Dextran), T06 (QCDCR) and T07 (QCDCR+CpG) compared to control and commercial vaccine (T02) groups. Calves in groups T03 and T04 experienced less clinical disease compared to the other groups. Overall, the data suggests that vaccines containing CpG's (T03, T04 and T07), such as the E modified P-class CpG, demonstrated an enhanced efficacy and these vaccines were more efficacious than the commercial vaccine.

Figure 6:
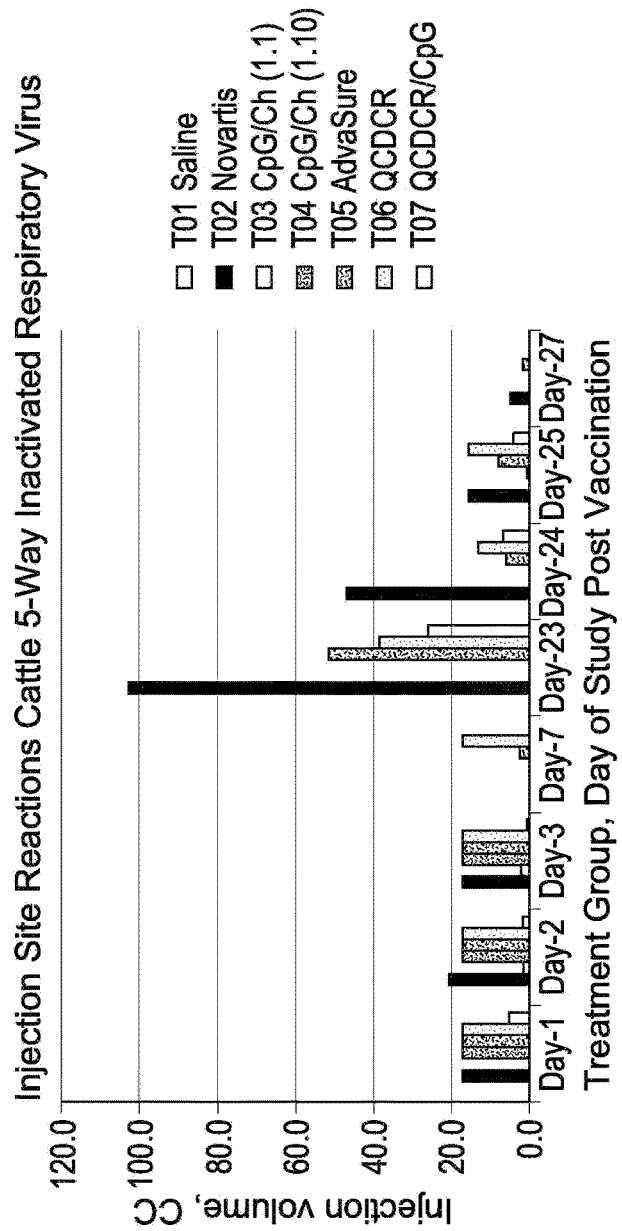
FIG. 6: Graph depicting the injection site reactions in calves immunized with pentavalent inactivated viral vaccine BVDV 1&2, IBRV, PI3V and BRSV in the presence of CpG+cholesterol (at ratios of 1:1 or 1:10 CpG:cholesterol), Advasure-DEAE/Dextran, QCDCR or QCDCR+CpG. Some animals were immunized with commercial vaccine. Placebo animals received sterile saline. Table 1 depicts percentage of calves with clinical disease, fever, leucopenia or viremia following challenge with BVDV-2 post vaccination with pentavalent inactivated viral vaccine BVDV 1&2, IBRV, PI3V and BRSV in the presence of CpG+cholesterol (at ratios of 1:1 or 1:10 CpG:cholesterol), Advasure-DEAE/Dextran, QCDCR or QCDCR+CpG. Some animals were immunized with commercial vaccine. Placebo animals received sterile saline.

The injection site reactions that developed following administration of the adjuvants are shown in FIG. 6a. The commercial vaccine (T02) and the Advasure-DEAE/Dextran (T05) vaccines were more reactive than the other vaccines tested. The vaccines containing QCDCR+CpG (T07) and CpG+cholesterol (T03 and T04) were the safest. In calves immunized with CpG+cholesterol, all symptoms of BVDV-2 challenge were reduced compared to non-vaccinated control animals.

The first vaccine dose administered induced low level serum neutralizing antibody titers. All the vaccines tested induced 100% sera-conversion to BVDV 1 and IBRV antigens by day 42. All vaccines tested, except the Advasure-DEAE/Dextran (T05) vaccine, induced a 100% sero-conversion to BVDV 2 by day 42. The Advasure-DEAE/Dextran (T05) vaccine induced 83% sero-conversion on day 42. Following challenge, BVDV 1 and BVDV 2 antibody responses were boosted to significantly higher levels in all groups (Table 2).

TABLE 2

| | part A | | | | | | part B | | |
| --- | --- | --- | --- | --- | --- | --- | --- | --- | --- |
| | BVDV 2 SN titers | | | BVDV 1 SN titers | | | IBR (BHV-1) SN titers | | |
| Group | Day 22 | 42 | 56 | Day 22 | 42 | 56 | Day 22 | 42 | 56 |
| T01 | 1.4 | 1.0 | 109.6 | 1.2 | 1.0 | 5.8 | 1.0 | 1.0 | 1.0 |
| | (0/7) | (0/7) | (5/7) | (0/7) | (0/7) | (2/7) | (0/7) | (0/7) | (0/7) |
| T02 | 2.9 | 211.5 | 18207.5 | 1.8 | 76.3 | 3119.4 | 3.1 | 110.4 | 78.1 |
| | (2/7) | (7 of 7) | (7 of 7) | (0 of 7) | (7 of 7) | (7 of 7) | (6 of 7) | (7 of 7) | (7 of 7) |
| T03 | 2.3 | 69.3 | 4783 | 3.4 | 163.9 | 3530.5 | 2.0 | 7.8 | 7.2 |
| | (0 of 7) | (7 of 7) | (7 of 7) | (0 of 7) | (7 of 7) | (7 of 7) | (6 of 7) | (7 of 7) | (7 of 7) |
| T04 | 3.2 | 129.2 | 11979.8 | 10.8 | 371.1 | 8823.7 | 2.1 | 10.3 | 8.4 |
| | (0 of 7) | (7 of 7) | (7 of 7) | (7 of 7) | (7 of 7) | (7 of 7) | (5 of 7) | (7 of 7) | (7 of 7) |
| T05 | 1.7 | 16.6 | 2598.3 | 3.4 | 362.4 | 8689.6 | 20.3 | 100.7 | 63.3 |
| | (0 of 7) | (5 of 6) | (6 of 6) | (2 of 7) | (6 of 6) | (6 of 6) | (7 of 7) | (6 of 6) | (6 of 6) |
| T06 | 3.1 | 153.6 | 17379.6 | 15.1 | 1217.7 | 24346.5 | 3.9 | 67 | 46.2 |
| | (0 of 7) | (7 of 7) | (7 of 7) | (4 of 7) | (7 of 7) | (7 of 7) | (6 of 7) | (7 of 7) | (7 of 7) |
| T07 | 6.7 | 228.3 | 20162.6 | 25.5 | 1103 | 19972.2 | 5.0 | 57.9 | 41 |
| | (3 of 7) | (7 of 7) | (7 of 7) | (7 of 7) | (7 of 7) | (7 of 7) | (7 of 7) | (7 of 7) | (7 of 7) |

SN—Serum Neutralization

The respective primary vaccination (T02-T07) primed BVDV-specific IgG antibody responses which were augmented by the booster vaccination and by BVDV2 challenge. There were no significant differences between IgG titers between the groups.

All the vaccine formulations were immunogenic and induced serum neutralization (BVDV 1 and BVDV 2) and IgG BVDV specific antibodies which were boosted by revaccination and challenge. Protection against BVDV challenge is by cell-mediated immunity (CMI; IFNγ secretion and activation of BVDV-specific CD4+ and CD8+ T cells), although antibody can neutralize free virus and hence protect against challenge if present at high levels, e.g. in colostrum fed to calves at birth. CMI (Th-1 type) responses were detected by secretion of IFNγ cytokine in vitro and humoral (Th-2 type) responses were determined by detecting for IL-4.

BVDV 1 and BVDV 2 antigens induced low level IFNγ responses and there were no significant differences ($P > 0.1$) between the treatment groups (data not shown). The BSRV antigen induced IFNγ responses in all groups except in groups T01 (saline) and T03 (CpG:cholesterol 1:1). The IBR antigen induced the strongest IFNγ responses in T05 (Advasure-DEAE/Dextran) and T06 (QCDCR) on all days tested post-vaccination and weak but positive responses in T02 (commercial vaccine), T04 (CpG:cholesterol 1:10), and T07 (QCDCR+CpG). The PI3 antigen induced IFNγ responses in T02 (commercial vaccine), T05 (Advasure-DEAE/Dextran), T06 (QCDCR) and T07 (QCDCR+CpG).

Example 3

Immunogenicity in Swine of a Subunit (Pertactin) *Bordetella bronchiseptica* Vaccine Formulated with Different Adjuvants Antigen-specific immune response of pigs immunized with pertactin (p68) formulated with various adjuvants, including CpG+cholesterol, were evaluated.

The Investigational Veterinary Products (IVP) used in the study were as follows: Vaccines were administered in 1-mL doses. Treatment Group T01 received 20 mM phosphate buffered saline. Treatment Group T02 received a vaccine containing Quil A (250 μg), cholesterol (250 μg), dimethyl dioctadecyl ammonium bromide (DDA; 100 μg), Carbopol® (0.075%), N-(2-Deoxy-2-L-leucylamino-b-D-glucopyranosyl)-N-octadecyldodecanoylamide hydroacetate, also known by the trade name Bay R1005® (1,000 μg). This combination of components is herein referred to as QCDCR. The composition also contained CpG 23878 (250 μg) and pertactin (10 μg). Treatment Group T03 received a vaccine in containing cholesterol (2,500 μg), CpG 23877 (250 μg), and pertactin (10 μg). Treatment Group T04 received a vaccine in containing cholesterol (2,500 μg), CpG 23878 (250 μg), and pertactin (10 μgTreatment Group T05 received a vaccine in containing 6% aluminum as Al(OH)$_3$ and pertactin (10 μg).

Sixty-four (64) clinically healthy, high-health status pigs of both sexes were used in the study. Pigs or their dams had no history of vaccination against or exposure to *B. bronchiseptica*. None of the pigs had a positive pertactin titer (defined as >200) from serum collected on at the farm of origin, or on Day −1.

On Day 0, pigs were vaccinated in the left neck with a 1.0 mL dose given by IM injection. On Day 21, pigs were revaccinated with the same IVP and dose as before, administered into the right neck. Within one hour of each vaccination, pigs were observed by the Investigator or a qualified technician for immediate adverse events related to vaccination.

The primary outcome variable was serum pertactin antibody titers (total IgG). Serum samples were tested for pertactin antibodies using an ELISA. Nunc Maxisorp plates were coated with 50 ng/well of pertactin in carbonate buffer (pH 9.1). Plates were washed and blocked with 1×PBS with 0.05% Tween 20 and 1% non-fat dry milk (1 h, R/T). Serum samples, diluted in blocking buffer, were added to the plates, incubated (1 h, R/T), washed and incubated (1 h, R/T) with HRP conjugate (Bethyl goat anti-pig IgG (h+l)) diluted 1:1250 in blocking buffer. Following a final wash, ABTS (KPL 50-62-00) substrate was added and OD values read after a 12-minute incubation at R/T. Titers were calculated based on a cutoff of 20% of the OD value of a 1:1000 dilution of a positive control serum pool.

Serum samples from T01, T03, T04, T05, and T08 were also tested for pertactin-specific IgG1 and IgG2 antibodies using an ELISA. Nunc Maxisorp plates were coated with 50 ng/well of pertactin in carbonate buffer (pH 9.1). Plates were washed and blocked with 1×PBS with 0.05% Tween 20 and 1% non-fat dry milk (1 h, R/T). Sera samples, diluted in blocking buffer, were added to the plates, incubated (1 h, R/T), washed and incubated (1 h, R/T) with monoclonal antibodies (IgG1-Serotec MCA635 or IgG2-Sertec MCA636) diluted 1:100 in blocking buffer. Plates were incubated (1 h, R/T), washed and an anti-mouse HRP conjugate added (Jackson Laboratories) diluted 1:5000 in blocking buffer. Following a final wash, ABTS (KPL 50-62-00) substrate was added and OD values read after a 20-minute incubation at R/T. IgG1 titers were calculated based on a cutoff of 50% of the OD value of a 1:1000 dilution of a positive control serum pool. IgG2 titers were calculated based on a cutoff of an OD of 0.2.

PBMCs, harvested from the heparin blood samples, were tested for antigen specific IFN-γ production. The IFN-γ response was tested by ELISPOT (Th1) to determine the frequency of INF-γ secreting cells/million cells SFC/10$^6$ from PBMCs (after subtracting the background in the medium controls). Additionally, IFN-γ responses were adjusted based on the stimulation index (SI) of the pertactin-stimulated cells compared to the medium control. A stimulation index of at least 2× was required for the sample to be deemed positive.

Results and Discussion

Pigs were vaccinated at day 0 and 21 with the vaccines shown in Table 3.

TABLE 3

| Vaccine Group | Adjuvant (Dose) | Carrier |
| --- | --- | --- |
| T01 | None | None |
| T02 | CpG23878 (250 μg) | QCDCR |
| T03 | CpG23877 (1:10) | Cholesterol |
| T04 | CpG23878 (1:10) | Cholesterol |
| T05 | Alhydrogel | None |

Blood samples for PBMC isolation and serum samples were taken on day −1, day 7, day 20, day 28 and day 35 and analyzed. Serum samples were tested for total IgG, IgG1 and IgG2 antibodies using an ELISA to purified, LPS-free recombinant pertactin. Isotyping antibodies were obtained from Bethyl Labs or AbD Serotec.

Pertactin-specific IgG levels were increased in groups T02 (CpG+QCDCR), T03 (CpG 23877+cholesterol; 1:10) and T04 (CpG 23878+cholesterol; 1:10) compared to the other vaccines tested.

No post-vaccination adverse events were reported for the observation time immediately following vaccination. No observations of reactions being caused by vaccination were recorded. The pigs in treatment group T01 remained negative for pertactin ELISA antibodies throughout the study.

Figure 7:
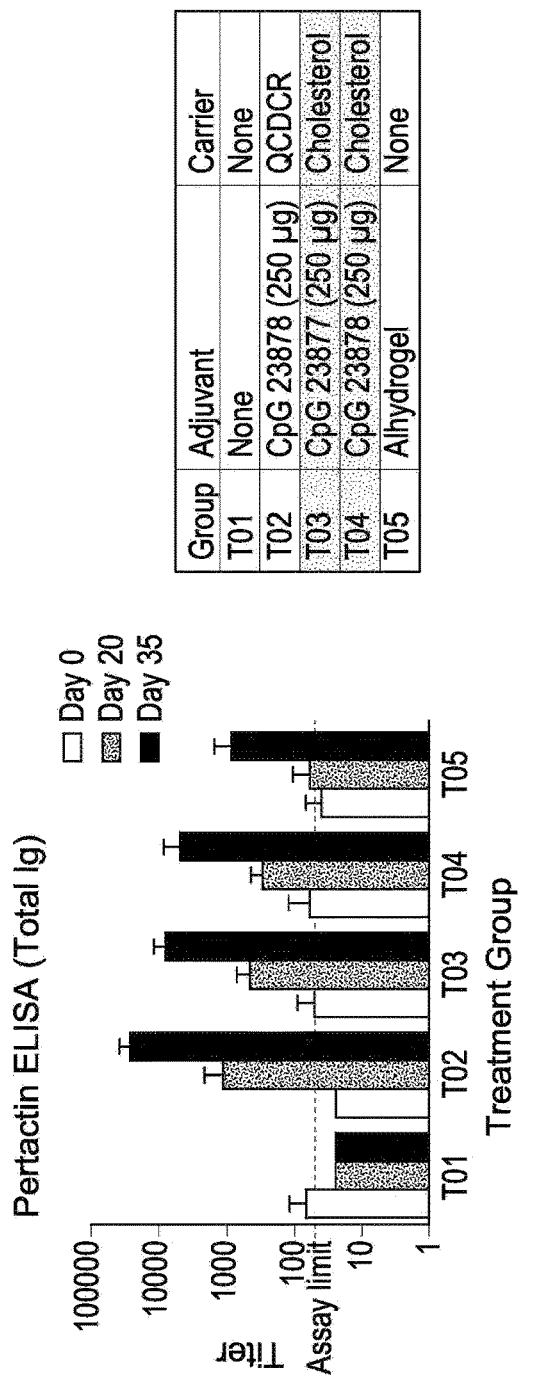
FIG. 7: Graph of antigen-specific antibody response in pigs immunized with pertactin (p68) formulated with various adjuvants including CpG+cholesterol.

All pigs had negative pertactin-specific ELISA titers 200) on Day −1. The percentage of pigs that ever seroconverted after vaccination was 0% for T01, 100% for T02, T03, T04, and T08. The treatment group (T02) with the CpG #23878 adjuvant and QCDCR carrier, had GMTs of 906.0 and 24728.5 on Days 20 and 35 respectively, and GMTs on both days were significantly higher (P≤0.10) than all other treatment groups (Tables 4 and 5). T01, the negative control, had means that were significantly lower than the other groups on both Days 20 and 35. The GMTs of T08 (formulated with aluminum hydroxide) were significantly lower than the GMTs of the pertactin vaccines formulated with the CpGs using the QCDCR or cholesterol carriers (T02, T03, T04) at both post-vaccination time points. A Graph of antigen-specific antibody response in pigs immunized with pertactin (p68) formulated with various adjuvants including CpG+cholesterol is presented in FIG. 7.

TABLE 4

Pertactin-specific Total IgG ELISA Titers Day 20
Geometric least squares means, standard errors, and ranges of antibody titers from pigs 20 days after being administered an IVP.

| Treatment Group | Adjuvant | Carrier | Geometric Mean | Standard Error | Range |
|---|---|---|---|---|---|
| T01 | None | None | 25.0$^a$ | 6.88 | 25 to 25 |
| T02 | CpG #23878 (250 µg) | QCDCR | 906.0$^b$ | 265.29 | 428 to 3188 |
| T03 | CpG#23877 (250 µg) | Cholesterol | 367.4$^c$ | 101.10 | 57 to 973 |
| T04 | CpG #23878 (250 µg) | Cholesterol | 254.2$^c$ | 69.97 | 66 to 473 |
| T05 | Alhydrogel | None | 46.5$^d$ | 12.79 | 25 to 163 |

$^{a,b,c,d}$geometric means with different superscripts are significantly different (P < 0.10)

TABLE 5

Pertactin-specific Total IgG ELISA Titers Day 35
Geometric least squares means, standard errors, and ranges of antibody titers from pigs 35 days after being administered an IVP.

| Treatment Group | Adjuvant | Carrier | Geometric Mean | Standard Error | Range |
|---|---|---|---|---|---|
| T01 | None | None | 25.0$^a$ | 5.79 | 25 to 25 |
| T02 | CpG #23878 (250 µg) | QCDCR | 24728.5$^b$ | 6077.46 | 10450 to 46473 |
| T03 | CpG #23877 (250 µg) | Cholesterol | 7608.8$^c$ | 1763.31 | 4619 to 17106 |
| T04 | CpG #23878 (250 µg) | Cholesterol | 4360.1$^d$ | 1010.43 | 1968 to 11829 |
| T05 | Alhydrogel | None | 625.6$^e$ | 144.97 | 233 to 1997 |

$^{a,b,c,d,e}$geometric means with different superscripts are significantly different (P ≤ 0.10)

Samples from only selected treatments were tested for isotype-specific pertactin serum antibody titers (Table 6). The IgG2/IgG1 ratio was 0.40 for T03 (CpG 23878 formulated with QCDCR) and 2.64 (CpG23878 formulated with cholesterol).

TABLE 6

Isotype-specific Pertactin Serum Antibody Titers

| | LS Geometric Mean Titer | | | | | | | | |
|---|---|---|---|---|---|---|---|---|---|
| | Day −1 | | | Day 20 | | | Day 35 | | |
| Trt | IgG1 | IgG2 | Ratio* | IgG1 | IgG2 | Ratio* | IgG1 | IgG2 | Ratio* |
| T01 | 29.7 | 25.0 | 0.84 | 25.0 | 25.0 | 1.00 | 25.0 | 25.0 | 1.00 |
| T02 | 29.3 | 25.0 | 0.85 | 76.9 | 51.4 | 0.67 | 3255.3 | 1316.1 | 0.40 |
| T03 | 36.5 | 25.0 | 0.68 | 33.6 | 89.3 | 2.66 | 767.7 | 2027.3 | 2.64 |
| T04 | 25.0 | 25.0 | 1.00 | 30.1 | 29.9 | 0.99 | 360.8 | 501.2 | 1.39 |
| T05 | 37.1 | 25.0 | 0.67 | 25.0 | 25.0 | 1.00 | 142.1 | 215.9 | 1.52 |

*IgG2/IgG1 ratio

The mean pertactin-specific IFN-γ responses was measured by Stimulation Index (SI) and spot-forming cells (SFC/10$^6$). There was considerable variability of the pertactin-specific IFN-γ responses of pigs within groups and between time points, in part because there were only 8 subjects per group. There were significant differences (P≤0.10) between treatments at all time points, including pre-vaccination (Day −1). For all post-vaccination time points (Days 7, 20, 28 and 35) the mean SI for T02 was significantly higher than T01 and T03. In contrast, the SI for T05 were not different from T01 on any post-vaccination time point. The SI for T04 was significantly higher than T01 on Days 20 and 35. The mean SFC/10$^6$ for T02 was significantly higher than T01 and T05 at 3 of 4 post-vaccination time points. The IFN-γ (SI and SFC/10$^6$) responses of 103 and T08 were not different from T01 at any post-vaccination time point.

Those skilled in the art will recognize, or be able to ascertain using no more than routine experimentation, many equivalents of the specific embodiments of the invention described herein. Such equivalents are intended to be encompassed by the following claims.

The invention claimed is:

1. A vaccine comprising one or more antigens and an adjuvant, the adjuvant consisting of one or more isolated immunostimulatory oligonucleotides and cholesterol admixed together, and wherein the one or more isolated immunostimulatory oligonucleotides comprises a modified internucleotide linkage or a modified nucleoside base and wherein said adjuvant consisting of one or more isolated immunostimulatory oligonucleotides and cholesterol admixed together is the sole adjuvant in the vaccine.

2. The vaccine of claim 1, wherein the one or more antigens are each independently, a microbial antigen, a self antigen, a tumor antigen, an allergen, or an addictive substance.

3. The vaccine of claim 2, wherein the one or more antigens are each independently, a peptide, a peptide conjugated to a carrier protein, a peptide conjugated to a virus-like particle, a polypeptide, a recombinant protein, a purified protein, whole killed pathogen, live attenuated virus or viral vector expressing an antigen, live attenuated bacteria or a bacterial vector expressing an antigen, a polysaccharide, a polysaccharide conjugated to a carrier protein, a hapten, a hapten conjugated to a carrier protein or a small molecule.

4. The vaccine of claim 3, wherein the antigen is of bacterial origin, viral origin or parasitic origin.

5. The vaccine of claim 4, wherein a) the bacterial antigen is whole killed bacteria, live attenuated bacteria or bacterial purified proteins; or b) the viral antigen is whole killed virus, live attenuated virus or viral purified proteins.

6. The vaccine of claim 3, wherein the carrier protein is a bacterial toxoid or derivative, Pseudomonas exotoxin, KLH or a virus-like particle.

7. The vaccine of claim 6, wherein a) the bacterial toxoid is diphtheria toxoid, or a derivative thereof; or b) the virus-like particle is HBsAg, HBcAg, *E. coli* bacteriophage Qβ, Norwalk virus or influenza HA.

8. The vaccine of claim 2, wherein a) the addictive substance is nicotine or a nicotine-like molecule; or b) the tumor antigen is one or more of survivin, Her-2, EFGRvIII, PSA, PAP or PMSA.

9. The vaccine of claim 3, wherein the hapten conjugated to a carrier protein is nicotine or a nicotine-like molecule conjugated to diphtheria toxoid or a derivative thereof.

10. The vaccine of claim 1, wherein the amount of cholesterol relative to the amount of antigen is 0.1 to 50 fold greater by weight, 1 to 10 fold greater by weight or equal in weight to the antigen.

11. A vaccine comprising one or more antigens and an adjuvant, the adjuvant consisting of an oil-containing emulsion, one or more isolated immunostimulatory oligonucleotides and cholesterol admixed together, and wherein the one or more isolated immunostimulatory oligonucleotides comprises a modified internucleotide linkage or a modified nucleoside base and wherein said adjuvant consisting of the oil-containing emulsion, said one or more isolated immunostimulatory oligonucleotides and cholesterol admixed together is the sole adjuvant in the vaccine.

12. The vaccine of claim 11, further comprising a pharmaceutical carrier.

13. The vaccine of claim 11, wherein the one or more antigens are each independently, a microbial antigen, a self antigen, a tumor antigen, an allergen, or an addictive substance.

14. The vaccine of claim 11, wherein the one or more antigens are each independently, a peptide, a polypeptide, a recombinant protein, a purified protein, whole killed pathogen, live attenuated virus or viral vector expressing an antigen, live attenuated bacteria or a bacterial vector expressing an antigen, a polysaccharide, a polysaccharide conjugated to a carrier protein, a hapten, a hapten conjugated to a carrier protein, or a small molecule.

15. The vaccine of claim 14, wherein the carrier protein is a bacterial toxoid or a derivative thereof, Pseudomonas exotoxin, KLH or a virus-like particle.

16. The vaccine of claim 15, wherein a) the bacterial toxoid or derivative is diphtheria toxoid or a derivative thereof; or b) the virus-like particle is HBsAg, HBcAg, *E. coli* bacteriophage Qβ, Norwalk virus or influenza HA.

17. The vaccine of claim 11, wherein the amount of cholesterol relative to the amount of antigen is 0.1 to 50 fold greater by weight, 1 to 10 fold greater by weight or equal in weight to the antigen.

18. The vaccine of claim 11, wherein the one or more immune modulatory molecules are each independently, a TLR agonist, an antimicrobial peptide, a cytokine, a chemokine or a NOD ligand.

19. The vaccine of claim 18, wherein the TLR agonists are each independently, an oligoribonucleotide (ORN), a small molecule that activates TLR 7 and/or TLR 8, or an oligodeoxynucleotide (ODN) that activates through TLR 9.

20. A method of inducing an antigen-specific immune response in a subject in need thereof, comprising administering a vaccine comprising one or more antigens and an adjuvant, the adjuvant consisting of an oil-containing emulsion, one or more isolated immunostimulatory oligonucleotides and cholesterol admixed together, in an effective amount to induce an antigen-specific immune response in the subject, and wherein the one or more isolated immunostimulatory oligonucleotides comprises a modified internucleotide linkage or a modified nucleoside base and wherein said adjuvant consisting of the oil-containing emulsion, said one or more isolated immunostimulatory oligonucleotides and cholesterol admixed together is the sole adjuvant in the vaccine.

* * * * *

SEQUENCE LISTING

<160> NUMBER OF SEQ ID NOS: 50

<210> SEQ ID NO 1

```
<211> LENGTH: 24
<212> TYPE: DNA
<213> ORGANISM: Artificial sequence
<220> FEATURE:
<223> OTHER INFORMATION: Synthetic sequence

<400> SEQUENCE: 1
tcgtcgtttt gtcgttttgt cgtt                                    24

<210> SEQ ID NO 2
<211> LENGTH: 21
<212> TYPE: DNA
<213> ORGANISM: Artificial sequence
<220> FEATURE:
<223> OTHER INFORMATION: Synthetic sequence

<400> SEQUENCE: 2
tcgtcgtttt tcggtgcttt t                                       21

<210> SEQ ID NO 3
<211> LENGTH: 24
<212> TYPE: DNA
<213> ORGANISM: Artificial sequence
<220> FEATURE:
<223> OTHER INFORMATION: Synthetic sequence

<400> SEQUENCE: 3
tcgtcgtttc gtcgttttgt cgtt                                    24

<210> SEQ ID NO 4
<211> LENGTH: 22
<212> TYPE: DNA
<213> ORGANISM: Artificial sequence
<220> FEATURE:
<223> OTHER INFORMATION: Synthetic sequence

<400> SEQUENCE: 4
tcgtcgtttt cggcggccgc cg                                      22

<210> SEQ ID NO 5
<211> LENGTH: 24
<212> TYPE: DNA
<213> ORGANISM: Artificial sequence
<220> FEATURE:
<223> OTHER INFORMATION: Synthetic sequence

<400> SEQUENCE: 5
tcgtcgtttt acggcgccgt cccg                                    24

<210> SEQ ID NO 6
<211> LENGTH: 23
<212> TYPE: DNA
<213> ORGANISM: Artificial sequence
<220> FEATURE:
<223> OTHER INFORMATION: Synthetic sequence

<400> SEQUENCE: 6
tcgtcgtttt cggcgcgcgc cgt                                     23

<210> SEQ ID NO 7
<211> LENGTH: 23
<212> TYPE: DNA
<213> ORGANISM: Artificial sequence
<220> FEATURE:
<223> OTHER INFORMATION: Synthetic sequence

<400> SEQUENCE: 7
```

-continued tcgtcgacga tcggcgcgcg ccg                                         23

<210> SEQ ID NO 8
<211> LENGTH: 23
<212> TYPE: DNA
<213> ORGANISM: Artificial sequence
<220> FEATURE:
<223> OTHER INFORMATION: Synthetic sequence

<400> SEQUENCE: 8
tcgacgtcga tcggcgcgcg ccg                                         23

<210> SEQ ID NO 9
<211> LENGTH: 24
<212> TYPE: DNA
<213> ORGANISM: Artificial sequence
<220> FEATURE:
<223> OTHER INFORMATION: Synthetic sequence

<400> SEQUENCE: 9
tcgacgtcga tcggcgcgcg ccgt                                        24

<210> SEQ ID NO 10
<211> LENGTH: 24
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: N is an iodo modified nucleotide
<220> FEATURE:
<221> NAME/KEY: misc_feature
<222> LOCATION: (2)..(2)
<223> OTHER INFORMATION: N is uracil

<400> SEQUENCE: 10
nncgacgtcg atcggcgcgc gccg                                        24

<210> SEQ ID NO 11
<211> LENGTH: 25
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: N is an iodo modified nucleotide
<220> FEATURE:
<221> NAME/KEY: misc_feature
<222> LOCATION: (2)..(2)
<223> OTHER INFORMATION: N is uracil

<400> SEQUENCE: 11
nncgacgtcg atcggcgcgc gccgt                                       25

<210> SEQ ID NO 12
<211> LENGTH: 23
<212> TYPE: DNA
<213> ORGANISM: Artificial sequence
<220> FEATURE:
<223> OTHER INFORMATION: Synthetic sequence

<400> SEQUENCE: 12
cgacgtcgat cggcgcgcgc cgt                                         23

```
<210> SEQ ID NO 13
<211> LENGTH: 24
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: N is an ethyl modified nucleotide
<220> FEATURE:
<221> NAME/KEY: misc_feature
<222> LOCATION: (2)..(2)
<223> OTHER INFORMATION: N is uracil

<400> SEQUENCE: 13
nncgacgtcg atcggcgcgc gccg                                          24

<210> SEQ ID NO 14
<211> LENGTH: 25
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: N is an iodo modified nucleotide
<220> FEATURE:
<221> NAME/KEY: misc_feature
<222> LOCATION: (2)..(2)
<223> OTHER INFORMATION: N is uracil

<400> SEQUENCE: 14
nncgtcgacg atcggcggcc gccgt                                         25

<210> SEQ ID NO 15
<211> LENGTH: 25
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: N is an iodo modified nucleotide
<220> FEATURE:
<221> NAME/KEY: misc_feature
<222> LOCATION: (2)..(2)
<223> OTHER INFORMATION: N is uracil

<400> SEQUENCE: 15
nncgtcgacg atcggcggcc gccgt                                         25

<210> SEQ ID NO 16
<211> LENGTH: 26
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: N is inosine
<220> FEATURE:
<221> NAME/KEY: misc_feature
<222> LOCATION: (3)..(3)
<223> OTHER INFORMATION: N is inosine
<220> FEATURE:
<221> NAME/KEY: misc_feature
<222> LOCATION: (5)..(5)
<223> OTHER INFORMATION: N is inosine
```

```
<220> FEATURE:
<221> NAME/KEY: misc_feature
<222> LOCATION: (7)..(7)
<223> OTHER INFORMATION: N is inosine
<220> FEATURE:
<221> NAME/KEY: misc_feature
<222> LOCATION: (9)..(9)
<223> OTHER INFORMATION: N is inosine
<220> FEATURE:
<221> NAME/KEY: misc_feature
<222> LOCATION: (11)..(11)
<223> OTHER INFORMATION: N is inosine
<220> FEATURE:
<221> NAME/KEY: misc_feature
<222> LOCATION: (13)..(13)
<223> OTHER INFORMATION: N is inosine
<220> FEATURE:
<221> NAME/KEY: misc_feature
<222> LOCATION: (15)..(15)
<223> OTHER INFORMATION: N is inosine
<220> FEATURE:
<221> NAME/KEY: misc_feature
<222> LOCATION: (17)..(17)
<223> OTHER INFORMATION: N is inosine
<220> FEATURE:
<221> NAME/KEY: misc_feature
<222> LOCATION: (19)..(19)
<223> OTHER INFORMATION: N is inosine
<220> FEATURE:
<221> NAME/KEY: misc_feature
<222> LOCATION: (21)..(21)
<223> OTHER INFORMATION: N is inosine
<220> FEATURE:
<221> NAME/KEY: misc_feature
<222> LOCATION: (23)..(23)
<223> OTHER INFORMATION: N is inosine
<220> FEATURE:
<221> NAME/KEY: misc_feature
<222> LOCATION: (25)..(25)
<223> OTHER INFORMATION: N is inosine

<400> SEQUENCE: 16 ncncncnc ncncncncnc ncncnc                                             26

<210> SEQ ID NO 17
<211> LENGTH: 21
<212> TYPE: DNA
<213> ORGANISM: Artificial sequence
<220> FEATURE:
<223> OTHER INFORMATION: Synthetic sequence

<400> SEQUENCE: 17
ggggacgacg tcgtgggggg g                                                21

<210> SEQ ID NO 18
<211> LENGTH: 21
<212> TYPE: DNA
<213> ORGANISM: Artificial sequence
<220> FEATURE:
<223> OTHER INFORMATION: Synthetic sequence

<400> SEQUENCE: 18
ggggacgacg tcgtgggggg g                                                21

<210> SEQ ID NO 19
<211> LENGTH: 24
<212> TYPE: DNA
<213> ORGANISM: Artificial sequence
<220> FEATURE:
<223> OTHER INFORMATION: Synthetic sequence

<400> SEQUENCE: 19
```
tcgtcgtttt gtcgttttgt cgtt                    24

<210> SEQ ID NO 20
<211> LENGTH: 24
<212> TYPE: DNA
<213> ORGANISM: Artificial sequence
<220> FEATURE:
<223> OTHER INFORMATION: Synthetic sequence

<400> SEQUENCE: 20
tcgtcgtttt gtcgtttttt tcga                    24

<210> SEQ ID NO 21
<211> LENGTH: 21
<212> TYPE: DNA
<213> ORGANISM: Artificial sequence
<220> FEATURE:
<223> OTHER INFORMATION: Synthetic sequence

<400> SEQUENCE: 21
tcgtcgtttt tcggtgcttt t                       21

<210> SEQ ID NO 22
<211> LENGTH: 21
<212> TYPE: DNA
<213> ORGANISM: Artificial sequence
<220> FEATURE:
<223> OTHER INFORMATION: Synthetic sequence

<400> SEQUENCE: 22
tcgtcgtttt tcggtcgttt t                       21

<210> SEQ ID NO 23
<211> LENGTH: 24
<212> TYPE: DNA
<213> ORGANISM: Artificial sequence
<220> FEATURE:
<223> OTHER INFORMATION: Synthetic sequence

<400> SEQUENCE: 23
tcgtcgtttt gtcgttttgt cgtt                    24

<210> SEQ ID NO 24
<211> LENGTH: 24
<212> TYPE: DNA
<213> ORGANISM: Artificial sequence
<220> FEATURE:
<223> OTHER INFORMATION: Synthetic sequence

<400> SEQUENCE: 24
tcgtcgtttc gtcgttttgt cgtt                    24

<210> SEQ ID NO 25
<211> LENGTH: 24
<212> TYPE: DNA
<213> ORGANISM: Artificial sequence
<220> FEATURE:
<223> OTHER INFORMATION: Synthetic sequence

<400> SEQUENCE: 25
tcgtcgtttt gtcgtttttt tcga                    24

<210> SEQ ID NO 26
<211> LENGTH: 22
<212> TYPE: DNA
<213> ORGANISM: Artificial sequence
<220> FEATURE:
<223> OTHER INFORMATION: Synthetic sequence

<400> SEQUENCE: 26
tcgcgtcgtt cggcgcgcgc cg                                              22

<210> SEQ ID NO 27
<211> LENGTH: 23
<212> TYPE: DNA
<213> ORGANISM: Artificial sequence
<220> FEATURE:
<223> OTHER INFORMATION: Synthetic sequence

<400> SEQUENCE: 27
tcgtcgacgt tcggcgcgcg ccg                                             23

<210> SEQ ID NO 28
<211> LENGTH: 21
<212> TYPE: DNA
<213> ORGANISM: Artificial sequence
<220> FEATURE:
<223> OTHER INFORMATION: Synthetic sequence

<400> SEQUENCE: 28
tcggacgttc ggcgcgcgcc g                                               21

<210> SEQ ID NO 29
<211> LENGTH: 19
<212> TYPE: DNA
<213> ORGANISM: Artificial sequence
<220> FEATURE:
<223> OTHER INFORMATION: Synthetic sequence

<400> SEQUENCE: 29
tcggacgttc ggcgcgccg                                                  19

<210> SEQ ID NO 30
<211> LENGTH: 20
<212> TYPE: DNA
<213> ORGANISM: Artificial sequence
<220> FEATURE:
<223> OTHER INFORMATION: Synthetic sequence

<400> SEQUENCE: 30
tcgcgtcgtt cggcgcgccg                                                 20

<210> SEQ ID NO 31
<211> LENGTH: 20
<212> TYPE: DNA
<213> ORGANISM: Artificial sequence
<220> FEATURE:
<223> OTHER INFORMATION: Synthetic sequence

<400> SEQUENCE: 31
tcgacgttcg gcgcgcgccg                                                 20

<210> SEQ ID NO 32
<211> LENGTH: 18
<212> TYPE: DNA
<213> ORGANISM: Artificial sequence
<220> FEATURE:
<223> OTHER INFORMATION: Synthetic sequence

<400> SEQUENCE: 32
tcgacgttcg gcgcgccg                                                   18

<210> SEQ ID NO 33
<211> LENGTH: 18
<212> TYPE: DNA
<213> ORGANISM: Artificial sequence
<220> FEATURE:
<223> OTHER INFORMATION: Synthetic sequence

<400> SEQUENCE: 33
tcgcgtcgtt cggcgccg                                                   18

<210> SEQ ID NO 34
<211> LENGTH: 22
<212> TYPE: DNA
<213> ORGANISM: Artificial sequence
<220> FEATURE:
<223> OTHER INFORMATION: Synthetic sequence

<400> SEQUENCE: 34
tcgcgacgtt cggcgcgcgc cg                                              22

<210> SEQ ID NO 35
<211> LENGTH: 22
<212> TYPE: DNA
<213> ORGANISM: Artificial sequence
<220> FEATURE:
<223> OTHER INFORMATION: Synthetic sequence

<400> SEQUENCE: 35
tcgtcgtttt cggcgcgcgc cg                                              22

<210> SEQ ID NO 36
<211> LENGTH: 23
<212> TYPE: DNA
<213> ORGANISM: Artificial sequence
<220> FEATURE:
<223> OTHER INFORMATION: Synthetic sequence

<400> SEQUENCE: 36
tcgtcgacga tcggcgcgcg ccg                                             23

<210> SEQ ID NO 37
<211> LENGTH: 23
<212> TYPE: DNA
<213> ORGANISM: Artificial sequence
<220> FEATURE:
<223> OTHER INFORMATION: Synthetic sequence

<400> SEQUENCE: 37
tcgtcgacga tcggcgcgcg ccg                                             23

<210> SEQ ID NO 38
<211> LENGTH: 22
<212> TYPE: DNA
<213> ORGANISM: Artificial sequence
<220> FEATURE:
<223> OTHER INFORMATION: Synthetic sequence

<400> SEQUENCE: 38
tcgcgtcgtt cggcgcgcgc cg                                              22

<210> SEQ ID NO 39
<211> LENGTH: 23
<212> TYPE: DNA
<213> ORGANISM: Artificial sequence
<220> FEATURE:
<223> OTHER INFORMATION: Synthetic sequence

<400> SEQUENCE: 39
tcgtcgacgt tcggcgcgcg ccg                                    23

<210> SEQ ID NO 40
<211> LENGTH: 21
<212> TYPE: DNA
<213> ORGANISM: Artificial sequence
<220> FEATURE:
<223> OTHER INFORMATION: Synthetic sequence

<400> SEQUENCE: 40
tcggacgttc ggcgcgcgcc g                                      21

<210> SEQ ID NO 41
<211> LENGTH: 19
<212> TYPE: DNA
<213> ORGANISM: Artificial sequence
<220> FEATURE:
<223> OTHER INFORMATION: Synthetic sequence

<400> SEQUENCE: 41
tcggacgttc ggcgcgccg                                         19

<210> SEQ ID NO 42
<211> LENGTH: 20
<212> TYPE: DNA
<213> ORGANISM: Artificial sequence
<220> FEATURE:
<223> OTHER INFORMATION: Synthetic sequence

<400> SEQUENCE: 42
tcgcgtcgtt cggcgcgccg                                        20

<210> SEQ ID NO 43
<211> LENGTH: 20
<212> TYPE: DNA
<213> ORGANISM: Artificial sequence
<220> FEATURE:
<223> OTHER INFORMATION: Synthetic sequence

<400> SEQUENCE: 43
tcgacgttcg gcgcgcgccg                                        20

<210> SEQ ID NO 44
<211> LENGTH: 18
<212> TYPE: DNA
<213> ORGANISM: Artificial sequence
<220> FEATURE:
<223> OTHER INFORMATION: Synthetic sequence

<400> SEQUENCE: 44
tcgacgttcg gcgcgccg                                          18

<210> SEQ ID NO 45
<211> LENGTH: 18
<212> TYPE: DNA
<213> ORGANISM: Artificial sequence
<220> FEATURE:
<223> OTHER INFORMATION: Synthetic sequence

<400> SEQUENCE: 45
tcgcgtcgtt cggcgccg                                          18

<210> SEQ ID NO 46

```
<211> LENGTH: 22
<212> TYPE: DNA
<213> ORGANISM: Artificial sequence
<220> FEATURE:
<223> OTHER INFORMATION: Synthetic sequence

<400> SEQUENCE: 46
tcgcgacgtt cggcgcgcgc cg                                              22

<210> SEQ ID NO 47
<211> LENGTH: 22
<212> TYPE: DNA
<213> ORGANISM: Artificial sequence
<220> FEATURE:
<223> OTHER INFORMATION: Synthetic sequence

<400> SEQUENCE: 47
tcgtcgtttt cggcgcgcgc cg                                              22

<210> SEQ ID NO 48
<211> LENGTH: 22
<212> TYPE: DNA
<213> ORGANISM: Artificial sequence
<220> FEATURE:
<223> OTHER INFORMATION: Synthetic sequence

<400> SEQUENCE: 48
tcgtcgtttt cggcggccgc cg                                              22

<210> SEQ ID NO 49
<211> LENGTH: 24
<212> TYPE: DNA
<213> ORGANISM: Artificial sequence
<220> FEATURE:
<223> OTHER INFORMATION: Synthetic sequence

<400> SEQUENCE: 49
tcgtcgtttt acggcgccgt gccg                                            24

<210> SEQ ID NO 50
<211> LENGTH: 23
<212> TYPE: DNA
<213> ORGANISM: Artificial sequence
<220> FEATURE:
<223> OTHER INFORMATION: Synthetic sequence

<400> SEQUENCE: 50
tcgtcgtttt cggcgcgcgc cgt                                             23
```